(12) United States Patent
Dressler et al.

(10) Patent No.: US 10,034,753 B2
(45) Date of Patent: Jul. 31, 2018

(54) CUSTOMIZED PATIENT-SPECIFIC ORTHOPAEDIC INSTRUMENTS FOR COMPONENT PLACEMENT IN A TOTAL HIP ARTHROPLASTY

(71) Applicant: DePuy Synthes Products, Inc., Raynham, MA (US)

(72) Inventors: Matthew R. Dressler, Fort Wayne, IN (US); Jason T. Sherman, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 92 days.

(21) Appl. No.: 14/920,311

(22) Filed: Oct. 22, 2015

(65) Prior Publication Data

US 2017/0112628 A1 Apr. 27, 2017

(51) Int. Cl.
| | |
|---|---|
| A61F 2/34 | (2006.01) |
| A61F 2/36 | (2006.01) |
| A61B 17/16 | (2006.01) |
| A61B 17/17 | (2006.01) |

(52) U.S. Cl.
CPC ............ *A61F 2/34* (2013.01); *A61B 17/1666* (2013.01); *A61B 17/1668* (2013.01); *A61B 17/175* (2013.01); *A61B 17/1746* (2013.01); *A61F 2/3609* (2013.01); *A61F 2002/3652* (2013.01)

(58) Field of Classification Search
CPC .............. A61F 2/34; A61F 2002/3495; A61F 2002/3631; A61B 17/175
See application file for complete search history.

(56) References Cited

U.S. PATENT DOCUMENTS

| | | | |
|---|---|---|---|
| 3,698,017 | A | 10/1972 | Scales et al. |
| 3,840,904 | A | 10/1974 | Tronzo |
| 3,903,549 | A | 9/1975 | Deyerle et al. |
| 4,475,549 | A | 10/1984 | Oh et al. |
| 4,632,111 | A | 12/1986 | Roche et al. |
| 4,711,233 | A | 12/1987 | Brown |
| 4,715,860 | A | 12/1987 | Amstutz et al. |
| 4,800,874 | A | 1/1989 | David et al. |
| 5,007,936 | A | 4/1991 | Woolson et al. |
| 5,098,437 | A | 3/1992 | Kashuba et al. |

(Continued)

FOREIGN PATENT DOCUMENTS

| | | |
|---|---|---|
| CA | 2501041 A1 | 4/2004 |
| CA | 2505371 A1 | 5/2004 |

(Continued)

OTHER PUBLICATIONS

International Search Report, International Application No. PCT/US2016/051260, 2 pages.

(Continued)

*Primary Examiner* — Bruce E Snow
(74) *Attorney, Agent, or Firm* — Barnes & Thornburg LLP

(57) ABSTRACT

A system for use in conjunction with a hip prosthesis is shown. A customized patient-specific acetabular orthopedic surgical instrument and a customized patient-specific femoral orthopedic surgical instrument are disclosed. A method for fabricating and using the orthopedic surgical instruments is also disclosed. A method for using the customized patient-specific acetabular orthopedic surgical instrument is disclosed. A method for using the customized patient-specific femoral orthopedic surgical instrument is disclosed.

8 Claims, 21 Drawing Sheets

(56) References Cited

U.S. PATENT DOCUMENTS

| | | |
|---|---|---|
| 5,108,401 A | 4/1992 | Insall et al. |
| 5,133,660 A | 7/1992 | Fenick |
| 5,171,243 A | 12/1992 | Kashuba et al. |
| 5,320,529 A | 6/1994 | Pompa |
| 5,320,625 A | 6/1994 | Bertin et al. |
| 5,658,294 A | 8/1997 | Sederholm et al. |
| 5,768,134 A | 6/1998 | Swaelens et al. |
| 5,817,097 A | 10/1998 | Howard et al. |
| 5,824,085 A | 10/1998 | Sahay et al. |
| 5,931,870 A | 8/1999 | Cuckler et al. |
| 5,942,370 A | 8/1999 | Neckers et al. |
| 5,976,149 A | 11/1999 | Masini et al. |
| 6,019,766 A | 2/2000 | Ling et al. |
| 6,161,080 A | 12/2000 | Aouni et al. |
| 6,228,121 B1 | 5/2001 | Khalili |
| 6,264,698 B1 | 7/2001 | Lawes et al. |
| 6,273,891 B1 | 8/2001 | Masini |
| 6,327,491 B1 | 12/2001 | Franklin et al. |
| 6,344,043 B1 | 2/2002 | Pappas |
| 6,395,005 B1 | 5/2002 | Lovell |
| 6,427,698 B1 | 8/2002 | Yoon |
| 6,463,351 B1 | 10/2002 | Clynch |
| 6,738,657 B1 | 5/2004 | Franklin et al. |
| 6,944,518 B2 | 9/2005 | Roose |
| 6,953,480 B2 | 10/2005 | Mears et al. |
| 6,991,655 B2 | 1/2006 | Iversen |
| 7,534,263 B2 | 5/2009 | Burdulis, Jr. et al. |
| 7,559,931 B2 | 7/2009 | Stone |
| 7,618,451 B2 | 11/2009 | Berez et al. |
| 7,634,119 B2 | 12/2009 | Tsougarakis et al. |
| 7,651,501 B2 | 1/2010 | Penenberg et al. |
| 7,717,956 B2 | 5/2010 | Lang |
| 7,796,791 B2 | 9/2010 | Tsougarakis et al. |
| 7,824,181 B2 | 11/2010 | Sers |
| 7,981,158 B2 | 7/2011 | Fitz et al. |
| 8,133,234 B2 | 3/2012 | Meridew et al. |
| 8,175,683 B2 | 5/2012 | Roose |
| 8,808,302 B2 | 8/2014 | Roose |
| 9,168,048 B2 | 10/2015 | Roose |
| 2002/0007294 A1 | 1/2002 | Bradbury et al. |
| 2004/0204760 A1 | 10/2004 | Fitz et al. |
| 2004/0236424 A1 | 11/2004 | Berez et al. |
| 2005/0107799 A1 | 5/2005 | Graf et al. |
| 2005/0148843 A1 | 7/2005 | Roose |
| 2005/0234461 A1 | 10/2005 | Burdulis et al. |
| 2005/0267584 A1 | 12/2005 | Burdulis et al. |
| 2006/0129160 A1 | 6/2006 | Liu et al. |
| 2007/0106305 A1 | 5/2007 | Kao et al. |
| 2007/0198022 A1 | 8/2007 | Lang et al. |
| 2007/0276400 A1 | 11/2007 | Moore et al. |
| 2008/0009874 A1 | 1/2008 | Meridew et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0234665 A1 | 9/2008 | Godara et al. |
| 2008/0234685 A1 | 9/2008 | Gjerde |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2009/0088674 A1 | 4/2009 | Caillouette et al. |
| 2009/0131941 A1 | 5/2009 | Park et al. |
| 2009/0138020 A1 | 5/2009 | Park et al. |
| 2009/0149977 A1 | 6/2009 | Schendel |
| 2009/0163922 A1 | 6/2009 | Meridew et al. |
| 2009/0222014 A1 | 9/2009 | Bojarski et al. |
| 2009/0270868 A1 | 10/2009 | Park et al. |
| 2009/0307893 A1 | 12/2009 | Burdulis, Jr. et al. |
| 2010/0016984 A1 | 1/2010 | Trabish |
| 2010/0023015 A1 | 1/2010 | Park |
| 2010/0042105 A1 | 2/2010 | Park et al. |
| 2010/0082035 A1 | 4/2010 | Keefer |
| 2010/0087829 A1 | 4/2010 | Metzger et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0191244 A1 | 7/2010 | White et al. |
| 2010/0212138 A1 | 8/2010 | Carroll et al. |
| 2010/0217338 A1 | 8/2010 | Carroll et al. |
| 2010/0274253 A1 | 10/2010 | Ure |
| 2011/0015639 A1 | 1/2011 | Metzger et al. |
| 2011/0213431 A1 | 9/2011 | Fitz et al. |
| 2011/0224674 A1 | 9/2011 | White et al. |
| 2012/0123423 A1 | 5/2012 | Fryman |
| 2013/0046310 A1 | 2/2013 | Ranawat et al. |
| 2014/0336657 A1 | 11/2014 | Iannotti et al. |
| 2015/0148807 A1 | 5/2015 | Park |
| 2017/0164957 A1 | 6/2017 | Bojarski et al. |

FOREIGN PATENT DOCUMENTS

| | | |
|---|---|---|
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1729483 A | 2/2006 |
| CN | 1729484 A | 2/2006 |
| CN | 1913844 A | 2/2007 |
| CN | 101111197 A | 1/2008 |
| CN | 101711695 A | 5/2010 |
| DE | 2830566 A1 | 1/1989 |
| DE | 4219939 A1 | 12/1993 |
| EP | 645984 A1 | 4/1995 |
| EP | 756735 | 2/1997 |
| EP | 1486900 A1 | 12/2004 |
| EP | 1669033 A1 | 6/2006 |
| GB | 2426200 A | 11/2006 |
| JP | 2005-511238 A | 4/2005 |
| JP | 2010-82448 A | 4/2010 |
| KR | 2005072500 A | 7/2005 |
| KR | 2005084024 A | 8/2005 |
| TW | I231755 B | 5/2005 |
| WO | 1993025157 A1 | 12/1993 |
| WO | 9528688 A1 | 10/1995 |
| WO | 2001084479 A1 | 11/2001 |
| WO | 2005027755 A1 | 3/2005 |
| WO | 2004049981 A3 | 4/2005 |
| WO | 2005051239 A1 | 6/2005 |
| WO | 2005051240 A1 | 6/2005 |
| WO | 2005084558 A1 | 9/2005 |
| WO | 2006058057 A2 | 6/2006 |
| WO | 2006060795 A1 | 6/2006 |
| WO | 2007041375 A2 | 4/2007 |
| WO | 2007092841 A2 | 8/2007 |
| WO | 2007097854 A2 | 8/2007 |
| WO | 2007145937 A2 | 12/2007 |
| WO | 2008014618 A1 | 2/2008 |
| WO | 2008021494 A2 | 2/2008 |
| WO | 2008112996 A1 | 9/2008 |
| WO | 2009045960 A1 | 4/2009 |
| WO | 2009111512 A2 | 9/2009 |
| WO | 2009001083 A1 | 12/2009 |
| WO | 2012/021264 | 2/2012 |

OTHER PUBLICATIONS

International Search Report and Written Opinion, International Application No. PCT/US2016/057260, dated May 3, 2017, 10.

Berry, Seedhom, et al., "Personalised image-based templates for intra-operative guidance," Proceedings of the Institution of Mechanical Engineers, Part H: Journal of Engineering in Medicine, 111-118, 2005.

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—

(56) References Cited

OTHER PUBLICATIONS

Experimental Results and Aspects of Clinical Applications," Computer Assisted Orthopaedic Surgery, L.P. Nolte and R. Ganz, eds, 42-52, Hogrefe & Huber Publishing 1999.
PCT Search Report for International Application No. PCT/US2011/044466, filed Jul. 19, 2011, 4 pages.
Radermacher et al., "Computer Assisted Orthopaedic Surgery with Image Based Individual Templates", Clin Orthopaedics and Related Research 354, 28-38, 1998, 11 pages.
Hafez et al., "Computer-assisted Total Knee Arthroplasty Using Patient-Specific Templating", Clinical Orthopaedics and Related Research, 444, 184-192, 2006 (9 pages).
"Insall/Burstein II Surgical Technique", Constrained Condylar Modular Knee System, Zimmer, 1989, (18 pages).
PCT Search Report for Application PCT/US2008/078143, dated Dec. 19, 2008, (17 pages).
International Preliminary Report on Patentability for International Patent Publication No. PCT/US2008/078143, dated Apr. 15, 2010, 8 pages.
European Search Report for European Patent Application No. 10150487.6-2310, dated May 12, 2010, 7 pages.
European Search Report for European Patent Application No. 09171188.7-2310, dated Sep. 24, 2010, 7 pages.
Customized Patient Instruments, Patient specific instruments for patient specific needs, brochure. (2008) DePuy Orthopaedics, Inc. 14 sheets.
Customized Patient Instruments, Primary Cruciate Retaining Surgical Technique for use with the Sigma.RTM. Knee System Utilizing Specialist.RTM. 2 Instrumentation, brochure. (2008) DePuy Orthopaedics, Inc. pp. 1-23.
"TruMatch.TM. Personalized knee replacement solutions," tri-fold brochure. (2009) SIGMA.RTM. DePuy Orthopaedics, Inc. 2 pages.
Murphy, S.B., et al. "The Hip Sextant: Navigation of Acetabular Component Orientation Using a Mechanical Instrument," brochure. (2009) 1 page.
Seel et al. "Three-Dimensional Planning and Virtual Radiographs in Revision Total Hip Arthroplasty for Instability", Clinical Orthopaedics and Related Research, No. 442, pp. 35-38, Jan. 2006.
Radermacher, "Development of a Clinical Demonstrater for Computer Assisted Orthopedic Surgery with CT-Image Based Individual Templates (chapter in Computer Assisted Radiology and Surgery, edited by H.U. Lemke, M.W. Vannier and K. Inamura)," (1997).
Radermacher, "Clinical Experience With the Individual Template Technique," (2001).
Radermacher, "Computer Assisted Orthopedic Surgery by Means of Individual Templates Aspects and Analysis of Potential Applications," (1994).
Radermacher, German Version "Potentials of CT-based Planning and Template-based Procedure in Hip and Knee Surgery," (2000).
Radermacher, English Translation of German Version "Potentials of CT-based Planning and Template-based Procedure in Hip and Knee Surgery," (2000).
Patent Cooperation Treaty, International Preliminary Report on Patentability, International Application No. PCT/US2011/044466, dated Feb. 12, 2013, 10 Pages.
English translation of Japanese Search Report dated Feb. 24, 2015, 4 pages.
English translation of First Office Action issued by the State Intellectual Property Office, P.R. China, for Chinese Application No. 201180039293.9, dated Jan. 6, 2015, 10 pages.
English translation of Chinese Search Report for Chinese Application No. 201180039293.9, dated Dec. 28, 2014, 2 pages.
Biomet: Signature Hip Technology Personalized Patient Care, available online, accessed Feb. 23, 2016, 2 pages.

CUSTOMIZED PATIENT-SPECIFIC ORTHOPAEDIC INSTRUMENTS FOR COMPONENT PLACEMENT IN A TOTAL HIP ARTHROPLASTY

TECHNICAL FIELD

The present disclosure relates generally to customized patient-specific orthopaedic surgical instruments and more particularly to customized patient-specific acetabular orthopaedic surgical instruments and customized patient-specific femoral orthopaedic surgical instruments.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral stem orthopaedic prosthesis. A typical acetabular orthopaedic prosthesis includes an acetabular cup, which is secured to the patient's natural acetabulum, and an associated polymer/ceramic/metal bearing or ring. A typical femoral orthopaedic prosthesis includes a femoral stem, which is secured to the patient's femur.

To facilitate the replacement of the natural joint with an acetabular orthopaedic prosthesis, orthopaedic surgeons may use a variety of orthopaedic surgical instruments such as, for example, reamers, drill guides, drills, and/or other surgical instruments. Typically, such orthopaedic surgical instruments are generic with respect to the patient such that the same orthopaedic surgical instrument may be used on a number of different patients during similar orthopaedic surgical procedures.

SUMMARY

According to one aspect of the disclosure, a method of using a system for facilitating implantation of a hip prosthesis is disclosed. The method includes positioning a collar of a customized patient-specific femoral surgical instrument on a patient's femur bone such that (i) a negative contour defined in a bone-facing surface of the collar receives a corresponding positive contour of the patient's femur, and (ii) a top surface of the collar defines a resection plane for resecting the patient's femur, advancing a resection tool along the resection plane surface of the collar to remove one or more portions of the patient's femur, positioning a femoral stem component in the femur bone, and aligning the femoral stem component with an alignment guide coupled to the collar to position the femoral stem component in a predetermined position.

In some embodiments, the method further may include positioning a customized patient-specific acetabular surgical instrument on a patient's coxal bone such that a negative contour defined in the customized patient-specific acetabular surgical instrument receives a corresponding positive contour of the patient's coxal bone, positioning an acetabular cup component in the patient's coxal bone, and aligning the acetabular cup component with an alignment guide coupled to the body to position the acetabular cup component in predetermined position. In some embodiments, the method further may include determining the position of the customized patient-specific acetabular surgical instrument on the patient's coxal bone using one or more sensors located in the customized patient-specific acetabular surgical instrument. In some embodiments, the method further may include forming an assembled hip joint prosthesis by positioning a femoral head on the femoral stem component and inserting the femoral head into a cavity of the acetabular cup component, and determining the position of the patient's coxal bone relative to the patient's femur when the assembled hip joint prosthesis is implanted in the patient using one or more sensors positioned in the customized patient-specific acetabular surgical instrument and one or more sensors positioned in the customized patient-specific femoral surgical instrument. In some embodiments, the method further may include attaching a reaming guide housing and a reamer to the customized patient-specific acetabular surgical instrument, the reamer including one or more sensors positioned thereon, reaming an acetabular of the patient to a predetermined depth, and determining how much bone has been removed from the acetabulum by comparing the data received from the sensors of the reamer to the data received from the sensors of the customized patient-specific acetabular surgical instrument.

In some embodiments, the method further may include determining the position of the customized patient-specific femoral surgical instrument on the patient's femur using one or more sensors located in the collar. In some embodiments, the method further may include positioning the alignment guide on the collar of the customized patient-specific femoral surgical instrument after the patient's femur has been resected by the resection tool. In some embodiments, the method further may include broaching an intramedullary canal of the patient's femur using a reaming tool.

According to another aspect, an system for facilitating implantation of a hip prosthesis includes an acetabular cup component and a customized patient-specific acetabular surgical instrument. The acetabular cup component defining a cup axis extending away from the acetabular cup component. The customized patient-specific acetabular surgical instrument includes a body and an alignment guide. The body having (i) an inner surface defining a cylindrical passageway configured to receive the acetabular cup component, and (ii) a bone-facing surface having a customized patient-specific negative contour configured to receive a corresponding positive counter of the patient's coxal bone. The alignment guide coupled to the body, the alignment guide defining an alignment axis positioned to indicate a predetermined position of the acetabular cup component in the patient's coxal bone. In some embodiments, the alignment axis of the alignment guide is positioned according to a predetermined version angle and a predetermined inclination angle of the acetabular cup prosthesis.

In some embodiments, the acetabular cup component includes a base and a body extending away from the base, and the cup axis extends away from the acetabular cup component perpendicular to the base. In some embodiments, the customized patient-specific acetabular surgical instrument includes one or more sensors configured to determine a position of the customized patient-specific acetabular surgical instrument relative to the coxal bone, wherein each of the one or more sensors are positioned in the customized patient-specific acetabular surgical instrument based on a predetermined sensor position. In some embodiments, the one or more sensors cooperate with other sensors positioned on one or more surgical instruments and are configured to determine the position and orientation of the one or more surgical instruments relative to the position and orientation to the patient's femur. In some embodiments, the one or more sensors are configured to determine the position and an orientation of the customized patient-specific acetabular surgical instrument relative to a customized patient-specific femoral surgical instrument positioned on a patient's femur, wherein the customized patient-specific femoral surgical instrument includes one or more additional sensors configured to interact with the one or more sensors of the customized patient-specific acetabular surgical instrument.

In some embodiments, the system further may include a femoral stem component and a customized patient-specific femoral surgical instrument. The femoral stem component defining a trunnion axis extending along a trunnion and a neck of the femoral stem component. The customized patient-specific femoral surgical instrument including a collar and an alignment guide. The collar sized to fit around a neck of the patient's femur, the collar having: (i) a bone-facing surface having a customized patient-specific negative contour configured to receive a corresponding positive counter of the patient's femur, and (ii) top surface defining a resection plane surface configured to guide a surgical instrument as the patient's femur is resected. The alignment guide coupled to the collar, the alignment guide defining a femoral alignment axis positioned to indicate a predetermined angle of the femoral stem component. In some embodiments, the alignment guide of the customized patient-specific femoral surgical instrument is positioned to indicate a predetermined offset of the femoral stem component.

According to another aspect, a system for facilitating implantation of a hip prosthesis includes a femoral stem component and a customized patient-specific femoral surgical instrument. The femoral stem component defining a trunnion axis extending along a trunnion and a neck of the femoral stem component. The customized patient-specific femoral surgical instrument includes a collar and an alignment guide. The collar sized to fit around a neck of the patient's femur, the collar having: (i) a bone-facing surface having a customized patient-specific negative contour configured to receive a corresponding positive counter of the patient's femur, and (ii) top surface defining a resection plane surface configured to guide a surgical instrument as the patient's femur is resected. The alignment guide coupled to the collar, the alignment guide defining a femoral alignment axis positioned to indicate a predetermined angle of the femoral stem component.

In some embodiments, the collar comprises a first collar segment and a second collar segment connected by a hinge, the hinge defining a hinge axis, and wherein the first collar segment and the second collar segment are configured to rotate about the hinge axis to allow the customized patient-specific femoral surgical instrument to advance onto the patient's femur. In some embodiments, the alignment axis of the alignment guide indicates a predetermined offset of the femoral stem component from the patient's femur and indicates a predetermined angle of the femoral stem component relative to the patient's femur.

In some embodiments, the customized patient-specific femoral surgical instrument includes one or more sensors. The one or more sensors positioned in the collar and configured to determine a position of the customized patient-specific femoral surgical instrument relative to the patient's femur, where the one or more sensors are positioned in the customized patient-specific femoral surgical instrument based on a predetermined sensor position.

BRIEF DESCRIPTION OF THE DRAWINGS

The detailed description particularly refers to the following figures, in which.

DETAILED DESCRIPTION OF THE DRAWINGS

Figure 1:
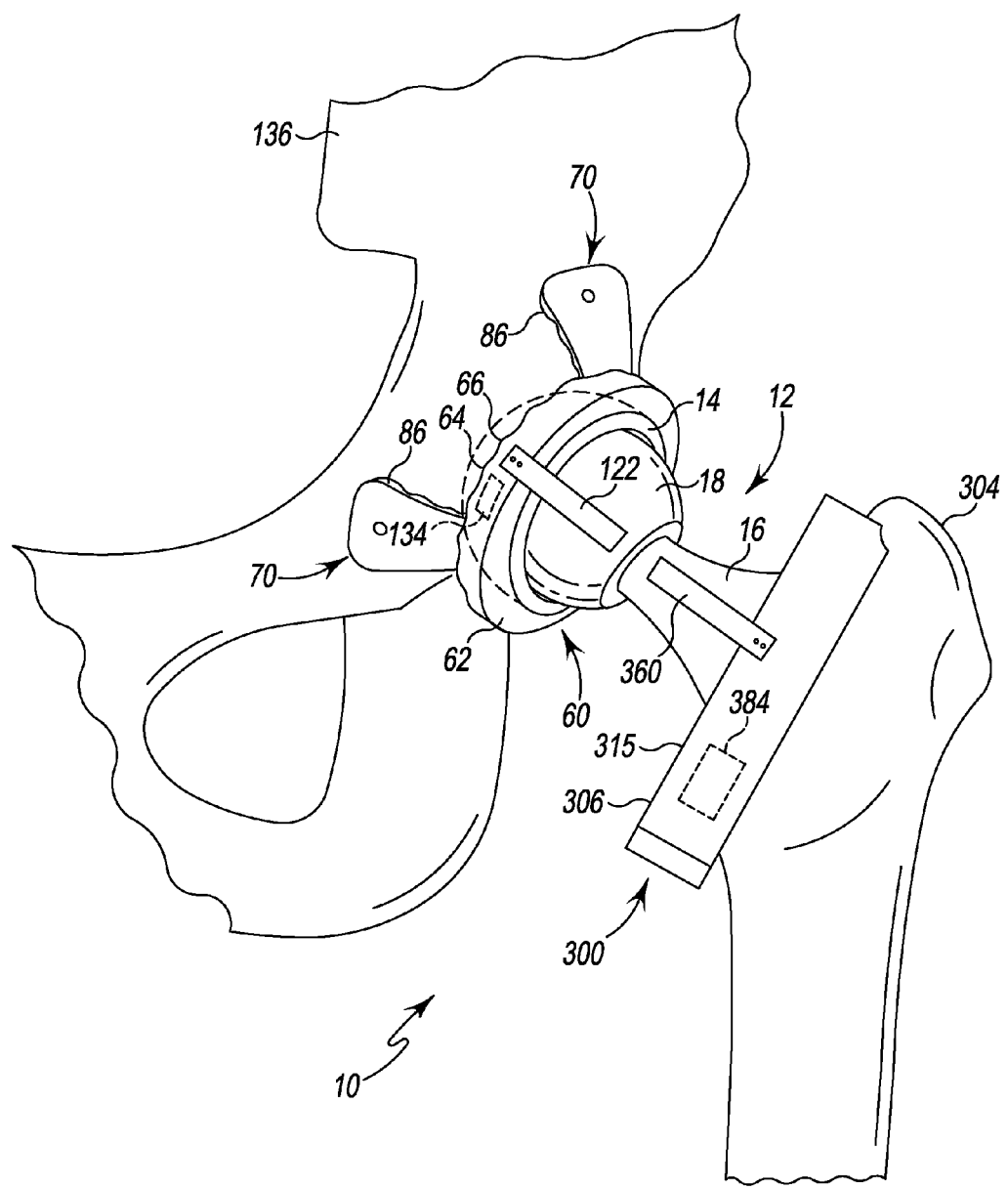
FIG. 1 is a perspective view of an embodiment of a surgical system and an embodiment of a hip joint prosthesis installed in the body of a patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring to FIG. 1, a surgical instrument system 10 used in conjunction with a hip joint prosthesis 12 is shown. The surgical instrument system 10 includes a customized patient-specific acetabular surgical instrument 60 (hereinafter "acetabular surgical instrument 60") and a customized patient specific femoral surgical instrument 300 (hereinafter "femoral surgical instrument 300"). The hip joint prosthesis 12 includes an acetabular cup 14, a femoral stem 16, and a femoral head 18. The acetabular cup 14 is configured to be positioned in the patient's surgically-prepared acetabulum of the coxal bone 136. The femoral stem 16 is configured to be implanted in the patient's surgically-prepared femur 304. When the hip joint prosthesis is assembled 12, the femoral head 18 is configured to be positioned on a trunnion of the femoral stem 16 and inserted into a cavity formed in the acetabular cup 14.

Figure 2:
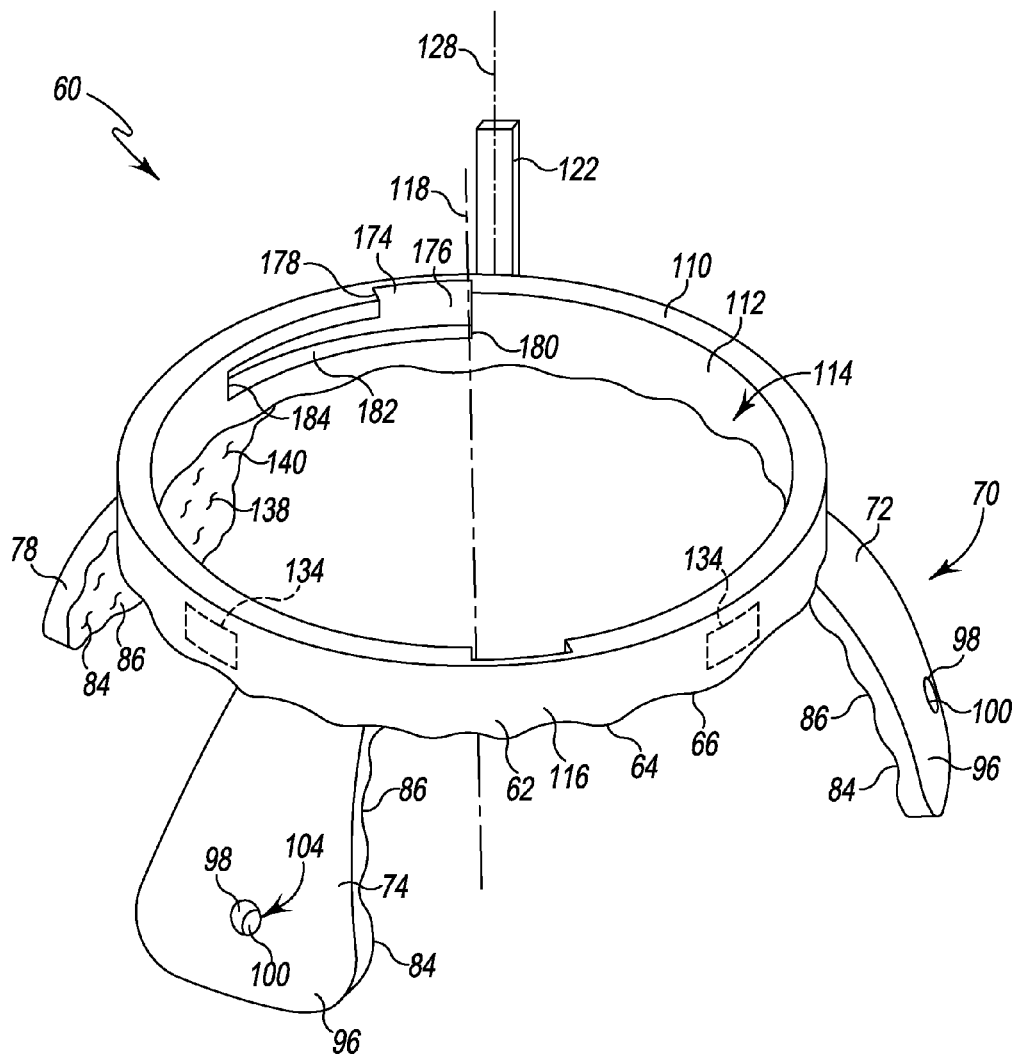
FIG. 2 is a perspective view of an embodiment of a customized patient-specific acetabular surgical instrument.

As shown in FIG. 2, the acetabular surgical instrument 60 includes a body 62 having a customized patient-specific negative contour 66 and one or more sensors 134 positioned on the body 62. In the illustrative embodiment, the acetabular surgical instrument 60 includes one or more arms 70, each of the arms 70 having a customized patient-specific negative contour 86. In other embodiments, the acetabular surgical instrument 60 does not include a plurality of arms 70. The acetabular surgical instrument 60 is configured to couple to the bony anatomy of the patient's coxal bone 136. Once coupled to the coxal bone 136, one or more surgical instruments may be attached to the acetabular surgical instrument 60 to assist the surgeon with the orthopaedic surgical operation. For example, a reamer 120 or a customized patient-specific alignment guide 122 may be attached to the acetabular surgical instrument 60. The alignment guide 122 of the acetabular surgical instrument 60 is configured to assist the surgeon in positioning the acetabular cup 14.

Figure 3:
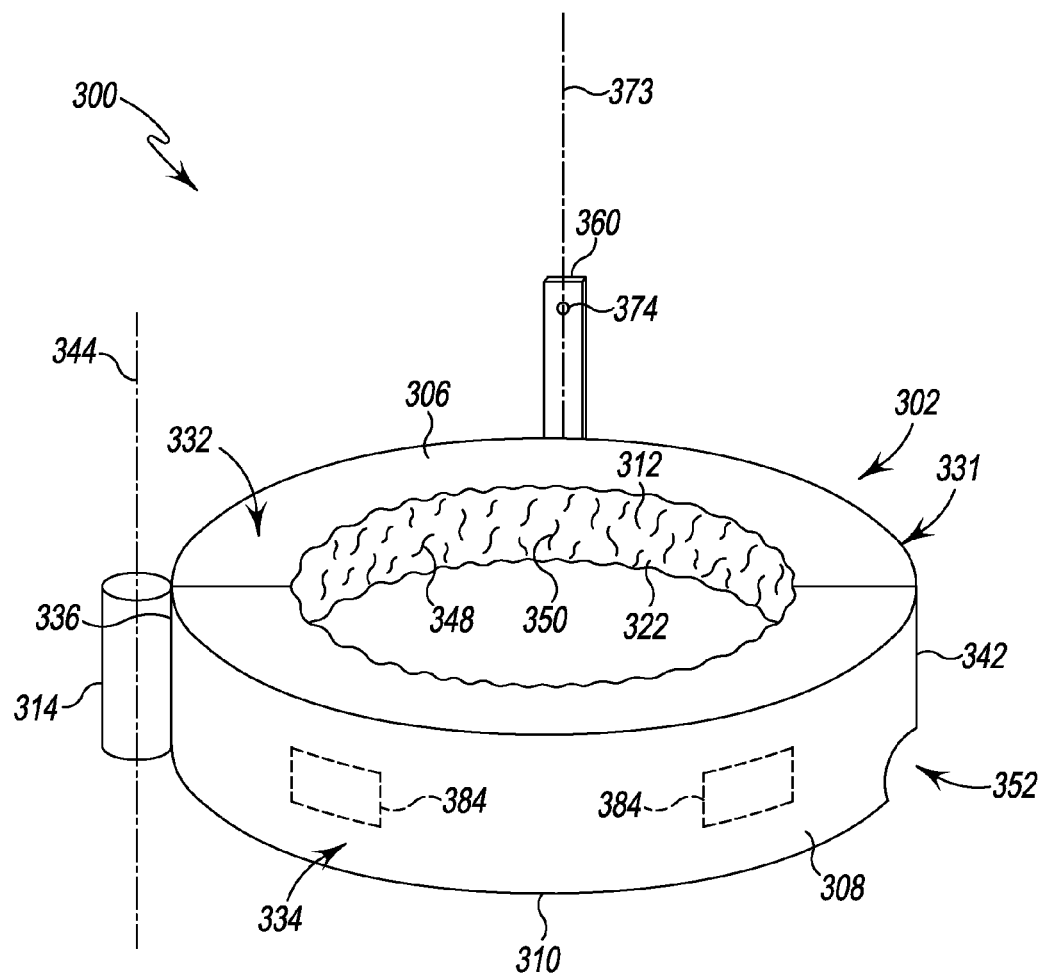
FIG. 3 is a perspective view of an embodiment of a customized patient-specific femoral surgical instrument.

As shown in FIG. 3, the femoral surgical instrument 300 includes a collar 302 having a customized patient-specific negative contour 322, a customized patient-specific alignment guide 360, and one or more sensors 384 positioned on the collar 302. The femoral surgical instrument 300 also includes a top surface 306 that defines a resection plane 315. The femoral surgical instrument 300 is configured to the bony anatomy of the patient's femur bone 304. Once coupled to the bone, the alignment guide 360 of the femoral surgical instrument 300 assists the surgeon in resecting the patient's femur bone 304 and positioning the femoral stem 16.

Each of the sensors 134, 384 are positioned in predetermined sensor locations in their respective surgical instruments 60, 300. Based on the predetermined sensor locations in the customized patient-specific surgical instruments 60, 300, the sensors 134, 384 are configured to provide a bone-coordinate reference frame for the patient's coxal bone 136 and the patient's femur 304 during an orthopaedic surgical procedure. Using the sensors 134, 384, the surgeon may determine the position of the femur 304 relative to the coxal bone 136. Based on this relative bone position information, a surgeon may be able to determine what range of motion and what kinematics a patient will likely experience after the orthopaedic surgery is complete. Additionally, other sensors may be positioned in orthopaedic components and other orthopaedic surgical instruments used during the orthopaedic surgical procedure. Using the sensors 134, 384 and these other sensors, the surgeon may determine the positions and orientations of the orthopaedic components and/or the other orthopaedic surgical instruments relative to the patient's bones 136, 304.

The illustrative embodiment of FIG. 1 shows the surgical instruments 60, 300 including alignment guides 122, 360 and sensors 134, 384. In some embodiments, the surgical instruments 60, 300 include the sensors 134, 384, but not the alignment guides 122, 360.

Figure 17:
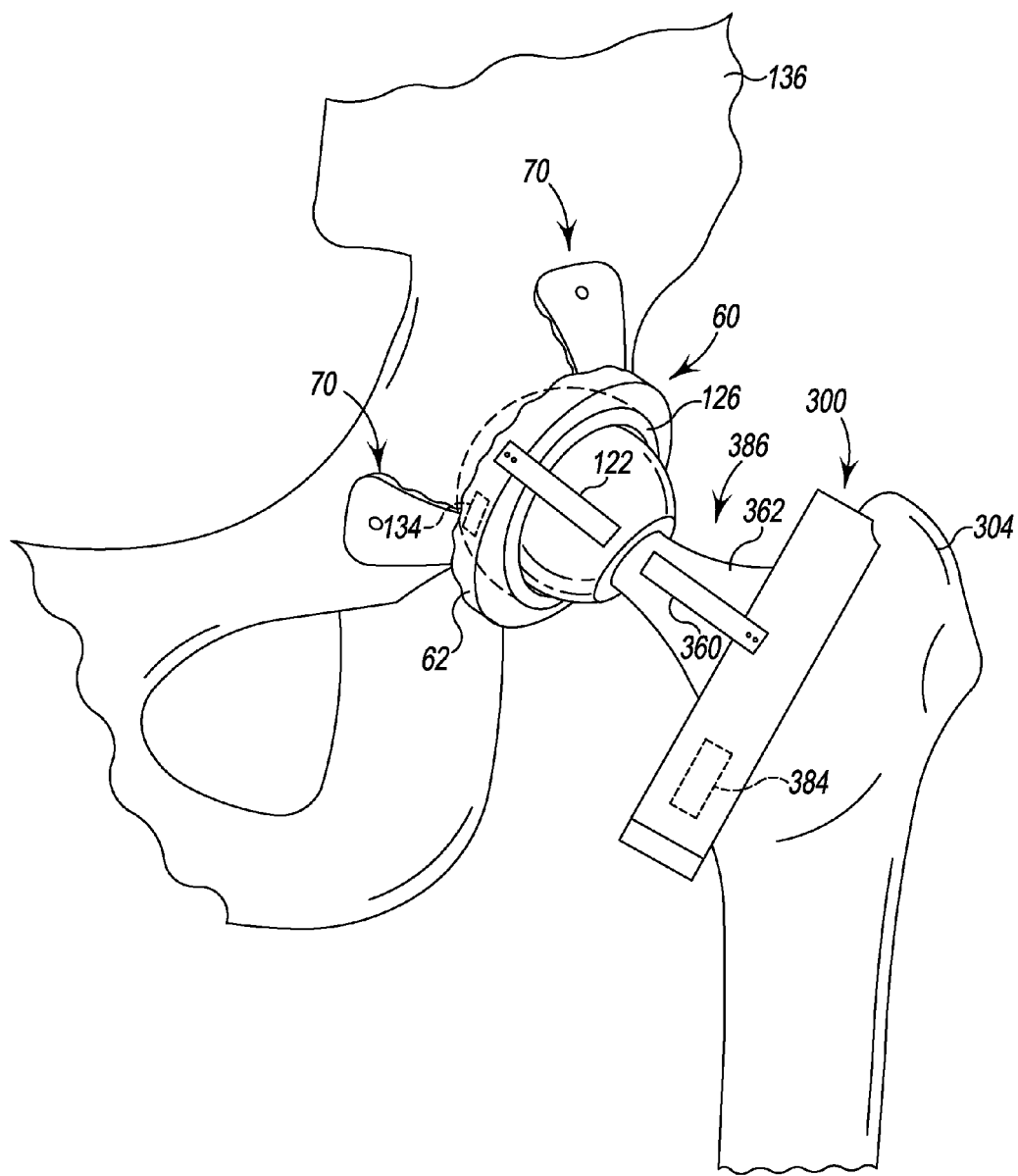
FIG. 17 is a perspective view of an assembled hip joint prosthesis with the customized patient-specific acetabular surgical instrument of FIG. 2 secured to the coxal bone of the patient and the customized patient-specific femoral surgical instrument of FIG. 3 secured to the femur bone of the patient.

Referring now to FIGS. 2 and 3, the pair of customized patient-specific orthopaedic surgical instruments of the surgical instrument system 10 cooperate to assist an orthopaedic surgeon to position orthopaedic hip components in a patient during an orthopaedic surgical operation, including implanting an orthopedic hip prosthesis in the patient. Specifically, the acetabular surgical instrument 60 is configured to assist the orthopaedic surgeon to position orthopaedic acetabular components 126 in a patient, and the femoral surgical instrument 300 is configured to assist the orthopaedic surgeon to position orthopaedic femoral stem components 362 in a patient. Furthermore, the pair of surgical instruments 60, 300 cooperate to verify the final position and orientation of the assembled orthopaedic hip prosthesis 386 in the patient as shown in FIG. 17.

In one particular embodiment, the surgical instruments 60, 300 are formed from a polymer or metal produced by additive manufacturing. In other embodiments, the surgical instruments 60, 300 are formed from injection-molded, clear polypropylene or other transparent material such that the interior of the surgical instruments 60, 300 are visible when the surgical instruments 60, 300 are secured to the patient's bony anatomy. In other embodiments, the surgical instruments 60, 300 may be formed from implant-grade metallic material such as titanium or cobalt chromium. Additionally, the surgical instruments 60, 300 may include image intensifiers such as, for example, stainless steel, tantalum, or other dense material to aid in positioning and to check the accuracy of alignment. For example, the surgical instruments 60, 300 may be configured to be radio-opaque and to provide markers in x-ray images taken of the patient.

Figure 5:
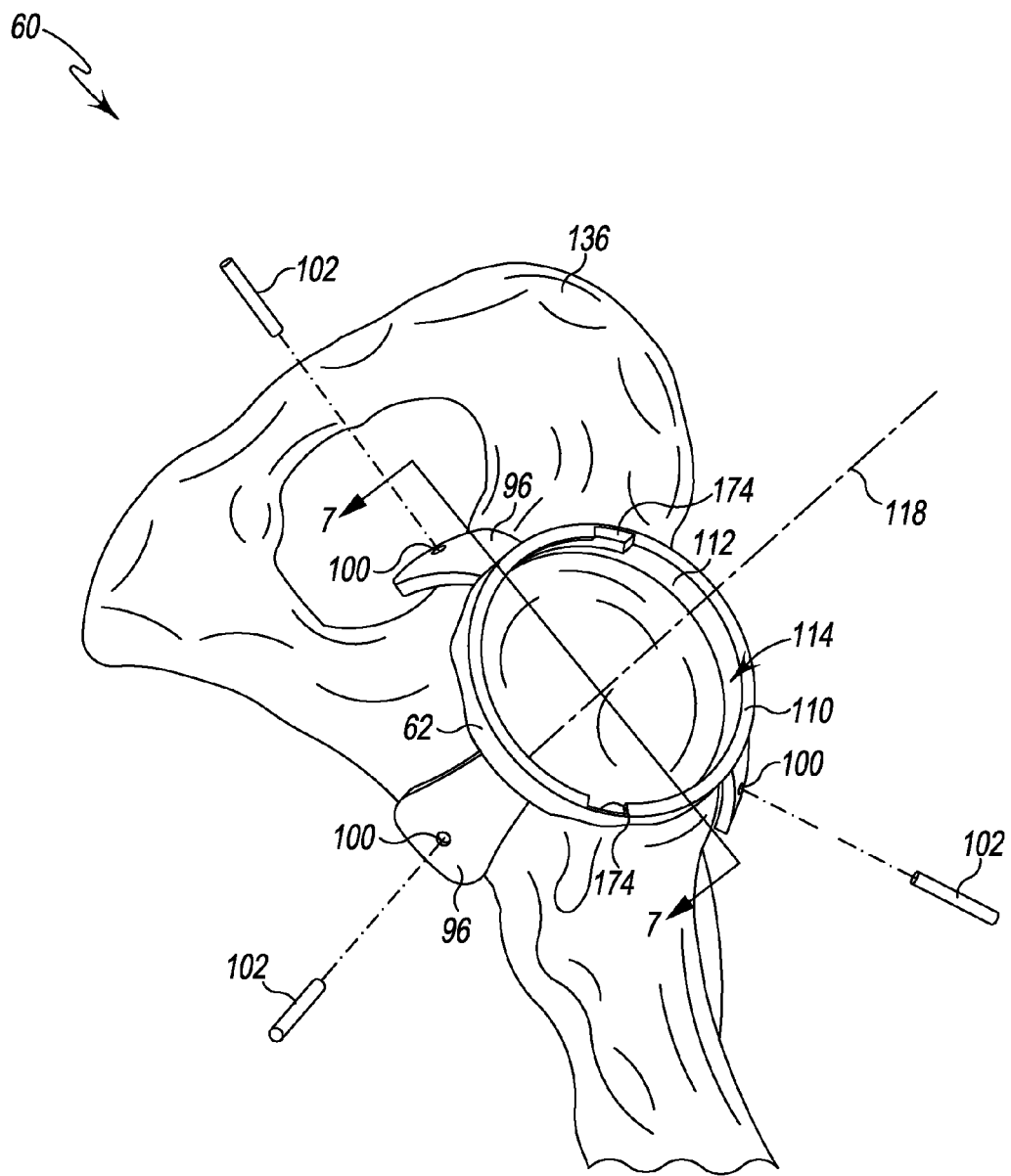
FIG. 5 is an exploded perspective view of the customized patient-specific acetabular surgical instrument of FIG. 2 positioned on a coxal bone.
Figure 6:
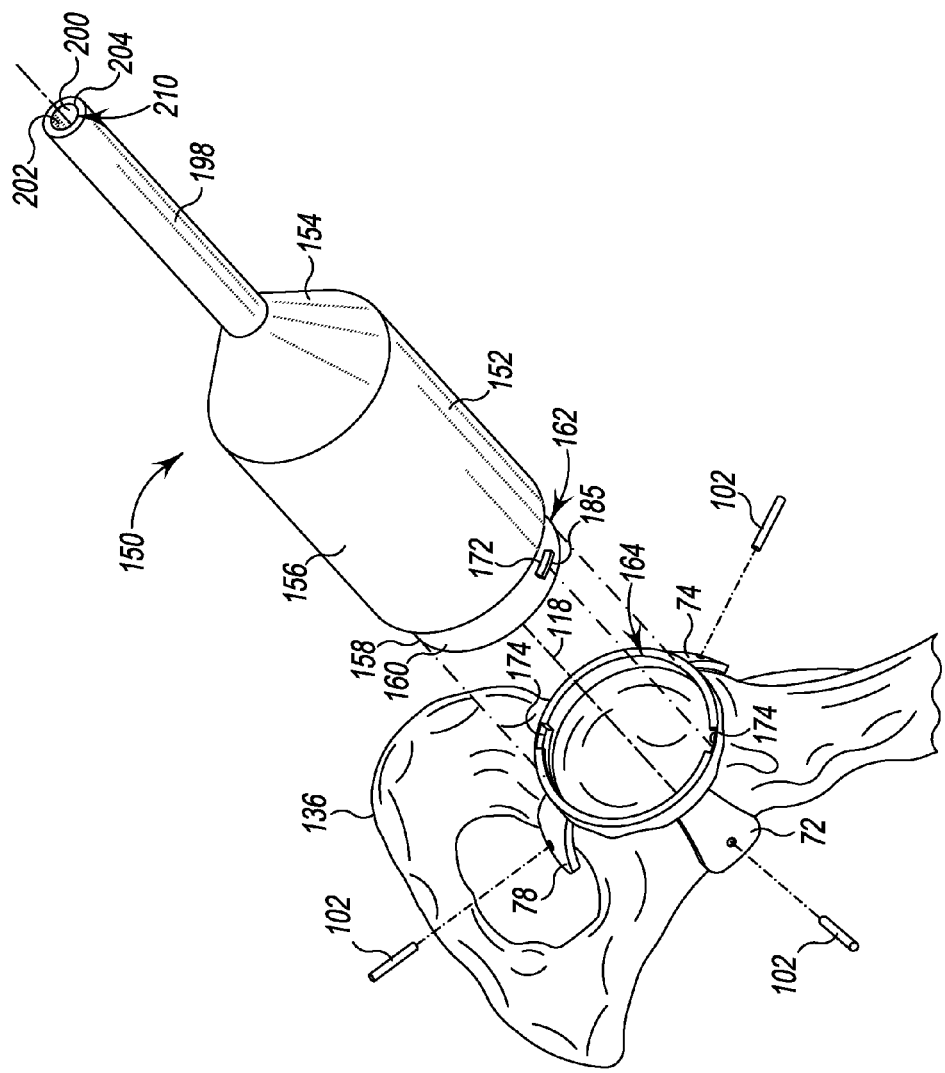
FIG. 6 is an exploded perspective view of the customized patient-specific acetabular surgical instrument of FIG. 2 and a guide housing.
Figure 7:
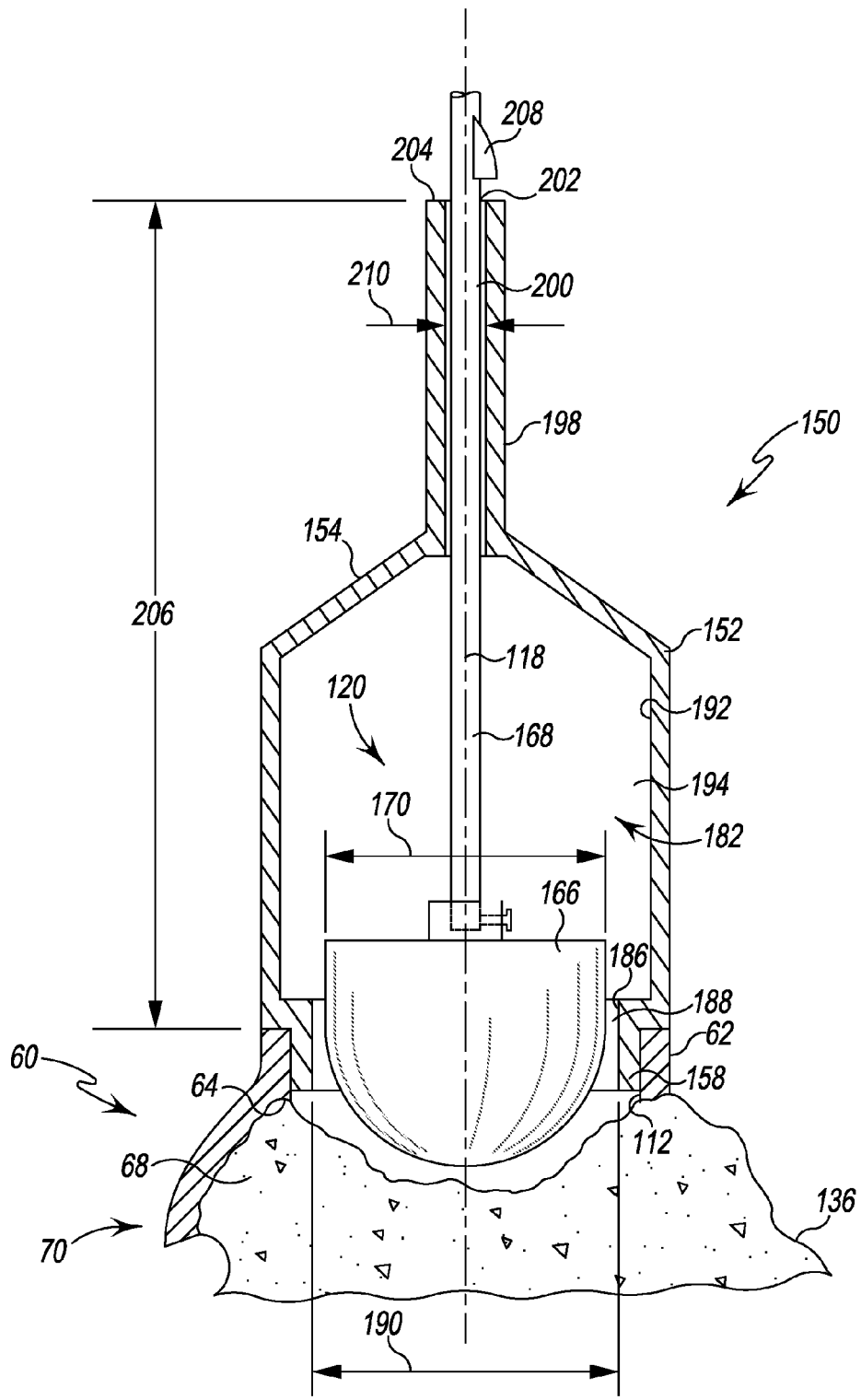
FIG. 7 is a sectional view of the customized patient-specific acetabular surgical instrument of FIG. 2, the housing and a reamer taken along the line 7-7.

Referring now to FIGS. 2 and 4-8, the acetabular surgical instrument 60 includes a guide body 62 configured to contact a portion of the patient's coxal bone 136 during use. In the illustrative embodiment, the guide body 62 has a generally ring shape but in other embodiments the guide body 62 could have a generally square shape, rectangular shape, or any other suitable form. As best seen in FIG. 7, the body 62 includes a bottom surface 64, which is configured to contact a portion of the area of the patient's coxal bone 136 proximate to the acetabulum. In the illustrative embodiment, the bottom surface 64 includes a customized patient-specific negative contour 66 configured to receive the corresponding positive contour of the acetabular margin 68 of the patient's coxal bone 136. It should be appreciated that in other embodiments the bottom surface 64 may include other customized patient-specific negative contours that are configured to receive other corresponding contours of the patient's coxal bone 136 proximate to the acetabulum.

The illustrative acetabular surgical instrument 60 also includes a plurality of arms 70 extending outwardly from the body 62. In other embodiments, the acetabular surgical instrument 60 does not include a plurality of arms 70. In the illustrative embodiment of FIG. 2, the body 62 and the arms 70 are formed as a single monolithic component. However, it should be appreciated that in other embodiments the body 62 and the arms 70 could each be formed from separate pieces. For example, the arms 70 may be separately secured to the body 62 via suitable fasteners such as screws, bolts, adhesive, or the like.

Figure 4:
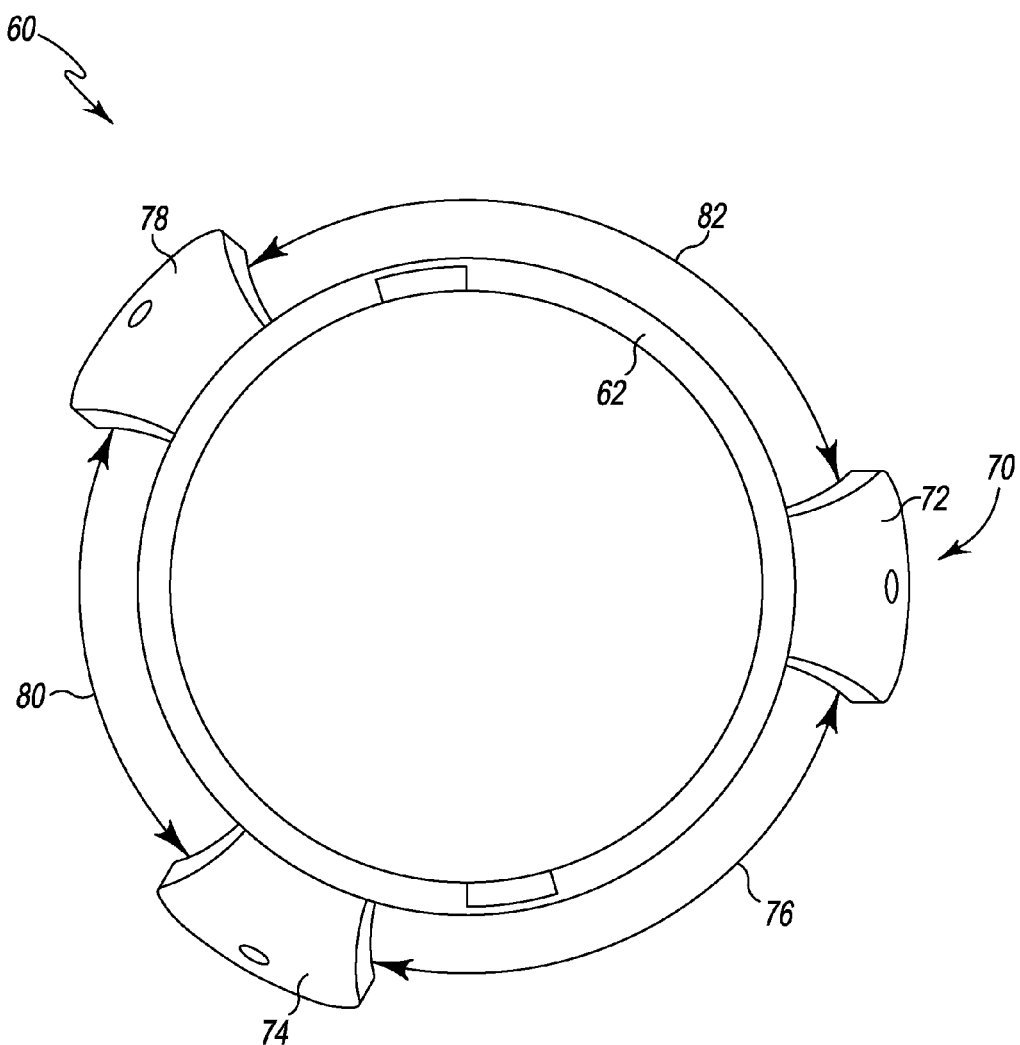
FIG. 4 is a top plan view of the acetabular surgical instrument of FIG. 2.

In the illustrative embodiment, the acetabular surgical instrument 60 includes three arms 70 extending from the body 62. In other embodiments, the acetabular surgical instrument 60 may include additional or fewer arms depending on the patient's bony anatomy and the preference of the surgeon. When viewed from the top plan view of FIG. 4, the arms 70 extend from the body 62 in a configuration that defines an angle between each arm 70. For example, as illustrated in FIG. 4, an arm 72 and an arm 74 define an angle 76 therebetween, the arm 74 and an arm 78 define an angle 80 therebetween, and the arm 72 and the arm 78 define an angle 82 therebetween. The magnitude of each of the angles 76, 80, 82 is equal to approximately 120 degrees. In one particular embodiment, the arms 70 may extend from the body 62 such that the each of the angles 76, 80, 82 has a magnitude different from any other angle. Like many other dimensional characteristics described herein, the magnitude of the angles 76, 80, 82 may be customized to as required for the particular patient.

Each arm 70 is configured to contact a portion of the patient's coxal bone 136 during use. Each arm 70 includes a bottom surface 84 that is configured to contact a portion of the area of the patient's coxal bone 136 proximate to the acetabulum. Each bottom surface 84 includes a customized patient-specific negative contour 86 configured to receive a portion of the corresponding contour of the patient's coxal bone 136 proximate to the acetabulum. In some embodiments, the arm 72 has a customized patient-specific negative contour 86 configured to receive the corresponding positive contour of the ilium of the patient's coxal bone 136. It should be appreciated that in other embodiments, the bottom surface 84 may include other customized patient-specific negative contours that are configured to receive other corresponding contours of the patient's coxal bone 136 proximate to the acetabulum. For example, the bottom surface 84 of another arm 70 may include a customized patient-specific negative contour configured to receive a corresponding contour of the pubis or the ischium of the patient's coxal bone 136. The negative contours 66, 86 include ridges 138 and depressions 140 that are configured to match corresponding the depressions and ridges of the patient's bony anatomy. The negative contours 66, 86 cooperate to ensure the acetabular surgical instrument 60 is placed on the patient's coxal bone 136 in a desired position and orientation, which is based on the predetermined inclination plane and the predetermined version plane of the acetabular orthopaedic prosthesis.

Each arm 70 includes a top surface 96 positioned opposite the bottom surface 84. Each arm 70 also includes an inner surface 98 that defines a passageway 100 extending through each arm 70. Each passageway 100 is sized to receive a corresponding bone pin 102 to be secured to the patient's coxal bone 136 as shown in FIG. 5. The bone pins 102 cooperate to lock the acetabular surgical instrument 60 in the unique position and orientation. It should be appreciated that in other embodiments the passageway 100 may be sized to receive wire or other retaining devices suitable for locking the acetabular surgical instrument 60 into place on the coxal bone 136.

As shown in FIG. 2, each passageway 100 is angled relative to the top surface 96 and the bottom surface 84. Each passageway 100 has a diameter 104 that is slightly larger than the outer diameter of the bone pin 102, and the passageway 100 of each arm 70 has a substantially circular cross-section. It should be appreciated that in other embodiments each arm 70 may include a passageway 100 configured to receive a bone pin with a different cross-sectional shape. It will also be appreciated that the passageway 100 may have any cross-sectional shape suitable for receiving a drill bit of a bone drill and passing a bone pin therethrough.

The guide body 62 includes a top surface 110 positioned opposite the bottom surface 64. An inner surface 112 connects the top surface 110 to the bottom surface 64 and defines an illustratively cylindrical passageway 114 extending therebetween. The guide body 62 also includes an outer surface 116 positioned opposite the inner surface 112. In some embodiments, the top surface 110 may be used to align the acetabular cup component 126 in the patient's coxal bone 136.

In the illustrative embodiment, the passageway 114 of the body 62 defines a longitudinal axis 118 that is oriented relative to the bottom surface 64 of the body 62 based on the predetermined version angle and the predetermined inclination angle of the acetabular cup prosthesis. As shown in FIGS. 2 and 7, the axis 118 extends generally perpendicular to the bottom surface 64. In other embodiments, the axis 118 may be angled in one or more directions relative to the bottom surface 64 depending on the predetermined inclination and version angles for the particular patient. As will be discussed in greater detail below, an acetabular reamer 120 is limited to movement along the axis 118 while being used to shape the patient's acetabulum. In that way, the acetabular surgical instrument 60 ensures that the patient's acetabulum is shaped to receive the acetabular cup prosthesis 126 according to the predetermined inclination and version angles.

Figure 8:
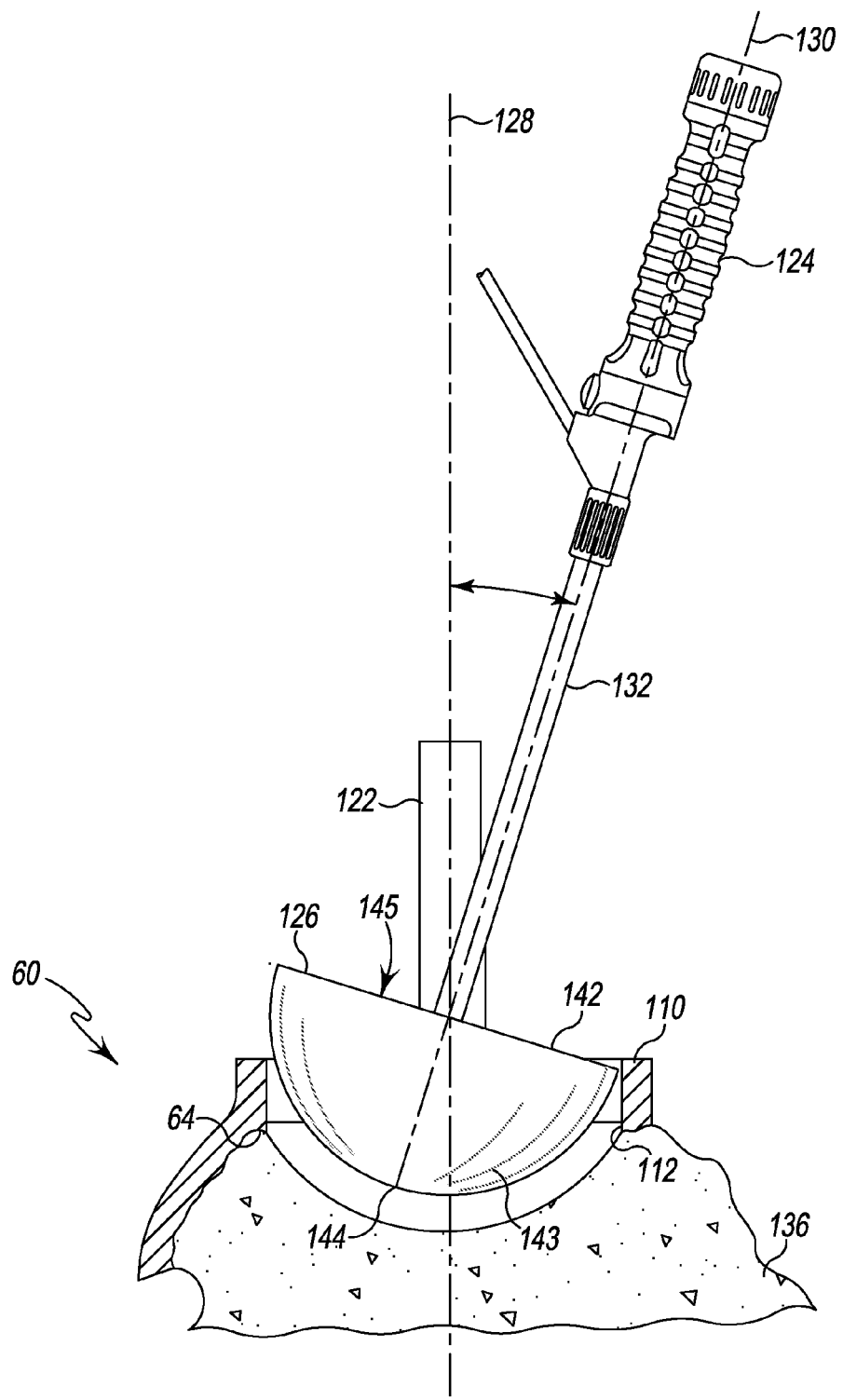
FIG. 8 is a sectional view of the customized patient-specific acetabular surgical instrument of FIG. 2 with an alignment guide taken along the line 7-7.

The acetabular surgical instrument 60 also includes an alignment guide 122 coupled to the guide body 62 as shown in FIGS. 2 and 8. The alignment guide 122 is configured to assist the orthopaedic surgeon in placing the orthopaedic acetabular components 126, such as an acetabular cup prosthesis or trialing component. The alignment guide 122 extends generally parallel to the axis 118 away from the top surface 110 of the acetabular surgical instrument 60 to provide a visual indicator of the planned position and orientation of the orthopaedic prosthesis. As part of the fabrication process of the customized patient-specific acetabular surgical instrument 60, the position and orientation of the alignment guide 122 is determined based on the planned position and orientation of the acetabular cup prosthesis 126, such as a predetermined version angle and the predetermined inclination. Using those predetermined values, the alignment guide 122 is designed to provide a visual reference for the orthopaedic surgeon when implanting the orthopaedic acetabular components 126.

The alignment guide 122 is configured to be removably coupled to acetabular surgical instrument 60. In this way, the alignment guide 122 can be removed to allow other surgical instruments to be attached to the acetabular surgical instrument 60, such as the reamer 120.

The alignment guide 122 is configured to cooperate with a surgical tool 124 to provide a visual indication of the position and orientation of the orthopaedic acetabular components 126. To accomplish this, the alignment guide 122 defines an alignment axis 128. The alignment axis 128 is oriented parallel to the alignment guide 122. In the illustrative embodiment of FIG. 8, the alignment axis 128 extends parallel to the longitudinal axis 118. In such an embodiment, the alignment axis 128 extends perpendicular relative to the bottom surface 64 of the body 62 based on the predetermined version angle and the predetermined inclination angle of the acetabular cup prosthesis 126. In other embodiments, the alignment axis 128 may be angled in one or more directions relative to the bottom surface 64 according to the predetermined inclination and version angles.

As shown in FIG. 8, the position and orientation of the acetabular cup component 126 may be compared to a predetermined position and orientation using the alignment guide 122. The acetabular cup component 126 includes a base 142 and sidewall 143. The sidewall 143 extends away from the base 142 and terminates in an apex 144. The base 142 and the sidewall 143 define a cavity 145 sized to receive the femoral head 18 of the hip joint prosthesis 12. The acetabular cup component 126 also defines a cup axis 130. The cup axis 130 extends outwardly from the apex 144 perpendicularly to the base 142. In the illustrative embodiment of FIG. 8, the cup axis 130 extends along the shaft of the surgical tool 124, where the surgical tool 124 is coupled to the acetabular cup component 126. In the illustrative embodiment, the acetabular cup component 126 is an acetabular cup prosthesis. In other embodiments, the acetabular cup component 126 may be a trialing component.

In some embodiments, the acetabular cup component 126, such as a trialing component, includes one or more sensors (not shown). The one or more sensors of the acetabular cup component 126 are configured to cooperate with the sensors 134 of the acetabular surgical instrument 60. The sensors of the acetabular cup component 126 and the sensors 134 of the acetabular surgical instrument 60 may be configured to cooperate to determine the position of the acetabular cup component 126 relative to the patient's coxal bone 136. In other embodiments, other acetabular components, such as the acetabular cup prosthesis, include one or more sensors that cooperate with the sensors 134 to determine the position and orientation of the acetabular components relative to the patient's coxal bone 136.

To position the acetabular cup component 126 in the predetermined position and orientation, the cup axis 130 should be aligned with the alignment axis 128. An orthopaedic surgeon is able to align these two axes 128, 130 by comparing the alignment guide 122 to the surgical tool 124. In such a manner, an orthopaedic surgeon is able to intraoperatively determine if the acetabular cup component 126 is positioned and oriented in the predetermined position and orientation. In some embodiments, the alignment guide 122 may include markings made on one or more of its surfaces to further provide visual indications of the predetermined position and orientation of the acetabular cup prosthesis 126.

As discussed above, the acetabular surgical instrument 60 also includes one or more sensors 134 positioned in the body 62 of the acetabular surgical instrument 60. The one or more sensors 134 are configured to indicate the location of the acetabular surgical instrument 60 to a computing device such as the computing device shown and described in U.S. Pat. No. 8,265,949, which is expressly incorporated herein by reference. The sensors 134 are positioned in the customized patient-specific acetabular surgical instrument 60 in specific locations based on the predetermined position and orientation of the acetabular cup prosthesis 126. The sensors 134 are configured to measure the relative orientation and position of the acetabular surgical instrument 60 to one or more other sensors positioned elsewhere. For example, the sensors 134 may cooperate with sensors 384 positioned in a customized patient-specific femoral surgical instrument 300 to determine the position of the acetabular surgical instrument 60 relative to the femoral surgical instrument 300. The sensors 134 may also be configured to provide a bone-coordinate reference frame that indicates the position and orientation of the patient's coxal bone 136. In illustrative embodiments, the sensors 134 cooperate with other sensors (e.g., sensors 384 of the femoral surgical instrument 300) to determine the position of the coxal bone 136 relative to the position of the femur 304. The sensors 134 may also be configured to cooperate with sensors positioned on other surgical instruments (e.g., reamer) or other orthopaedic components (e.g., trialing components) to validate the use of such equipment during an orthopaedic surgical procedure.

The one or more sensors 134 may be embodied as electromagnetic tracking devices. Each electromagnetic tracking device cooperates with a transmitter and uses orthogonal magnetic fields to determine the position and orientation of the tracking device. The transmitter includes three orthogonal coils that are pulsed in a sequence to produce an electromagnetic field. Each electromagnetic tracking device also includes three orthogonal coils configured to measure the electromagnetic field produced by the transmitter. A computing device determines the position and orientation of the electromagnetic tracking device by comparing the strength of the received signals to the electromagnetic field that was produced by the transmitter. In some embodiments, the computing device is positioned on the electromagnetic tracking device. In other embodiments, the computing device is independent from the electromagnetic tracking device.

In some embodiments, the one or more sensors 134 may be embodied as another type of position and orientation sensor, such as an accelerometer. In other embodiments, the one or more sensors 134 may be embodied as inertial measurement units (IMU) configured to determine the position and orientation of the sensors 134 using a combination of sensors (e.g., accelerometers, gyroscopes, and/or magnetometers).

In some embodiments, the sensors 134 may be embodied as a passive transponder, such as a radio-frequency identification (RFID) tag. In such an embodiment, an RFID reader transmits an RF signal, which powers the sensor 134, and causes the sensor 134 to transmit information back to the RFID reader via another RF signal. If an RFID tag is interrogated by multiple RFID readers, a process of triangulation may be used to determine the precise location of the RFID tag. The RFID readers are connected to a computing device, which processes the data received from the sensors 134 to determine the position of the acetabular surgical instrument 60.

In yet other embodiments, the one or more sensors 134 of the acetabular surgical instrument 60 may include more than one type of sensor on the same acetabular surgical instrument. For example, the acetabular surgical instrument 60 may include both an electromagnetic tracking device and an RFID tag.

The acetabular surgical instrument 60 may be configured to prepare the patient's acetabulum to receive an acetabular cup prosthesis 126. As shown in FIGS. 6 and 7, a housing 150 is configured to be secured to the guide body 62 of the acetabular surgical instrument 60. The housing 150 and the reamer 120 are just one example of the surgical tools that may be coupled to the acetabular surgical instrument 60. In other embodiments, other types of tool may be coupled to the acetabular surgical instrument 60.

The housing 150 has a cylindrical main body 152 extending from an upper end 154 to a lower end 156. A sleeve 158 extends outwardly from the lower end 156 and includes an outer surface 160. The outer surface 160 has a diameter 162 that is less than a diameter 164 of the passageway 114 of the guide body 62. When the housing 150 is secured to the acetabular surgical instrument 60, the sleeve 158 is positioned in the passageway 114. As shown in FIG. 7, the passageway 114 is sized such that the acetabular reamer 120 may be moved through the passageway 114 and placed into contact with the patient's acetabulum. The acetabular reamer 120 includes a reamer head 166 removably secured to a reamer shank 168. The diameter 164 of the cylindrical passageway 114 is larger than an outer diameter 170 of the reamer head 166 to allow the reamer head 166 to advance therethrough. One example of an illustrative acetabular reamer surgical tool useable with the acetabular surgical instrument 60 is the DePuy Quickset® Acetabular Grater System, which is commercially available from DePuy Synthes Products, Inc. of Warsaw, Ind. U.S.A.

The sleeve 158 includes a pair of flanges 172 projecting outwardly from the outer surface 160 of the sleeve 158 as shown in FIG. 6. The flanges 172 are spaced apart from the lower end 156 of the main body 152 and extend in an arc about the circumference of the sleeve 158.

The guide body 62 includes a pair of corresponding slots 174 defined therein that are configured to receive the flanges 172 as best shown in FIG. 2. Each slot 174 includes a notch 176 extending from an upper end 178 defined in the top surface 110 of the body 62 to a lower end 180 defined in the inner surface 112 of the body 62. Each slot 174 also includes a channel 182 defined in the inner surface 112 that extends from the lower end 180 of the notch 176 to a distal end 184. The length of the channel 182 substantially corresponds to the length of the flange 172. The channel 182 extends orthogonally to the longitudinal axis 118. However, in other embodiments the channel 182 may be tilted relative to the longitudinal axis 118 depending the desired position and orientation of the acetabular surgical instrument 60.

The slots 174 and the flanges 172 cooperate to secure the housing 150 to the acetabular surgical instrument 60. The housing 150 is aligned with the acetabular surgical instrument 60 such that each flange 172 is positioned to be received into a notch 176 of a corresponding slot 174. When the housing 150 is seated on the acetabular surgical instrument 60, a bottom 185 of each flange 172 contacts the lower end 180 of the notch 176. The housing 150 is then rotated about the longitudinal axis 118 to advance each flange 172 into the channel 182 of the corresponding slot 174 until an end of the flange 172 is placed in contact with the distal end 184 of the channel 182. In such a manner, the housing 150 is secured to the acetabular surgical instrument 60.

In other embodiments, the acetabular surgical instrument 60 and the housing 150 include a different number of flanges 172 and slots 174. In other embodiments, the housing 150 may be securable to the acetabular surgical instrument 60 by other methods. For example, the sleeve 158 may have an external thread and the body 62 may have a corresponding internal thread. In such embodiments, the sleeve 158 may be threaded onto the body 62. In other embodiments, the housing 150 may include a latching mechanism secured to the main body 152 that engages with the body 62. Similarly, the housing 150 may be secured to the body 62 via suitable fasteners such as screws, bolts, or the like. In other embodiments, the acetabular surgical instrument 60 is not configured to couple to the housing 150, and therefore does not include any slots 174 formed in the body 62 thereof.

As best shown in FIG. 7, the sleeve 158 includes an inner surface 186 that defines a lower passageway 188. The lower passageway 188 has a diameter 190 that is slightly larger than the outer diameter 170 of the reamer head 166 of the acetabular reamer 120. As such, the lower passageway 188 is sized such that the acetabular reamer 120 may be moved along the longitudinal axis 118 and placed into contact with the patient's acetabulum. The main body 152 includes an inner surface 192 that defines a central passageway 194 connected with the lower passageway 188. The central passageway 194 has a diameter 196 that is larger than the diameter 190 of the lower passageway 188. However, in other embodiments, the diameter 196 of the central passageway 194 may be substantially equal to the diameter 190 of the lower passageway 188.

A hollow shaft 198 extends upwardly from the upper end 154 of the main body 152. The shaft 198 includes an inner surface 200 that defines a cylindrical passageway 202 extending from a top end 204 of the shaft 198 to the upper end 154 of the main body 152. As shown in FIG. 7, the cylindrical passageway 202 is fluidly connected with the central passageway 194 of the main body 152. The cylindrical passageway 202 has an inner diameter 210 that is smaller than the diameters 190, 196 of the passageways 188, 194 and that is only slightly larger than the outer diameter 170 of the reamer shank 168 of the acetabular reamer 120.

The acetabular surgical instrument 60, the housing 150, and the reamer 120 cooperate to ream the patient's acetabulum to a predetermined depth. The main body 152 and the shaft 198 define a total length 206. The magnitude of the total length 206 is set based on the predetermined depth to which the orthopaedic surgeon plans to ream the patient's acetabulum. The top end 204 of the shaft 198 cooperates with a protrusion 208 positioned on the reamer shank 168 to ensure that the reamer head 166 does not advance beyond the predetermined depth.

In some embodiments, the reamer 120 includes one or more sensors (not shown) configured to cooperate with the sensors 134 of the acetabular surgical instrument 60. For example, the sensors of the reamer 120 may be positioned in the reamer head 166. The sensors of the reamer 120 and the sensors 134 of the acetabular surgical instrument 60 may cooperate to determine the amount of material the surgeon has reamed from the patient's coxal bone 136. For example, using the bone-coordinate reference frame established by the sensors 134, the sensors of the reamer 120 may be able to determine the position and orientation of the reamer 120 relative to the coxal bone 136 and how much material has been removed from the coxal bone 136 by the reamer 120. In other embodiments, other surgical instruments include one or more sensors that cooperate with the sensors 134 to validate the operation of those surgical instruments during the orthopaedic surgical procedure.

Figure 9:
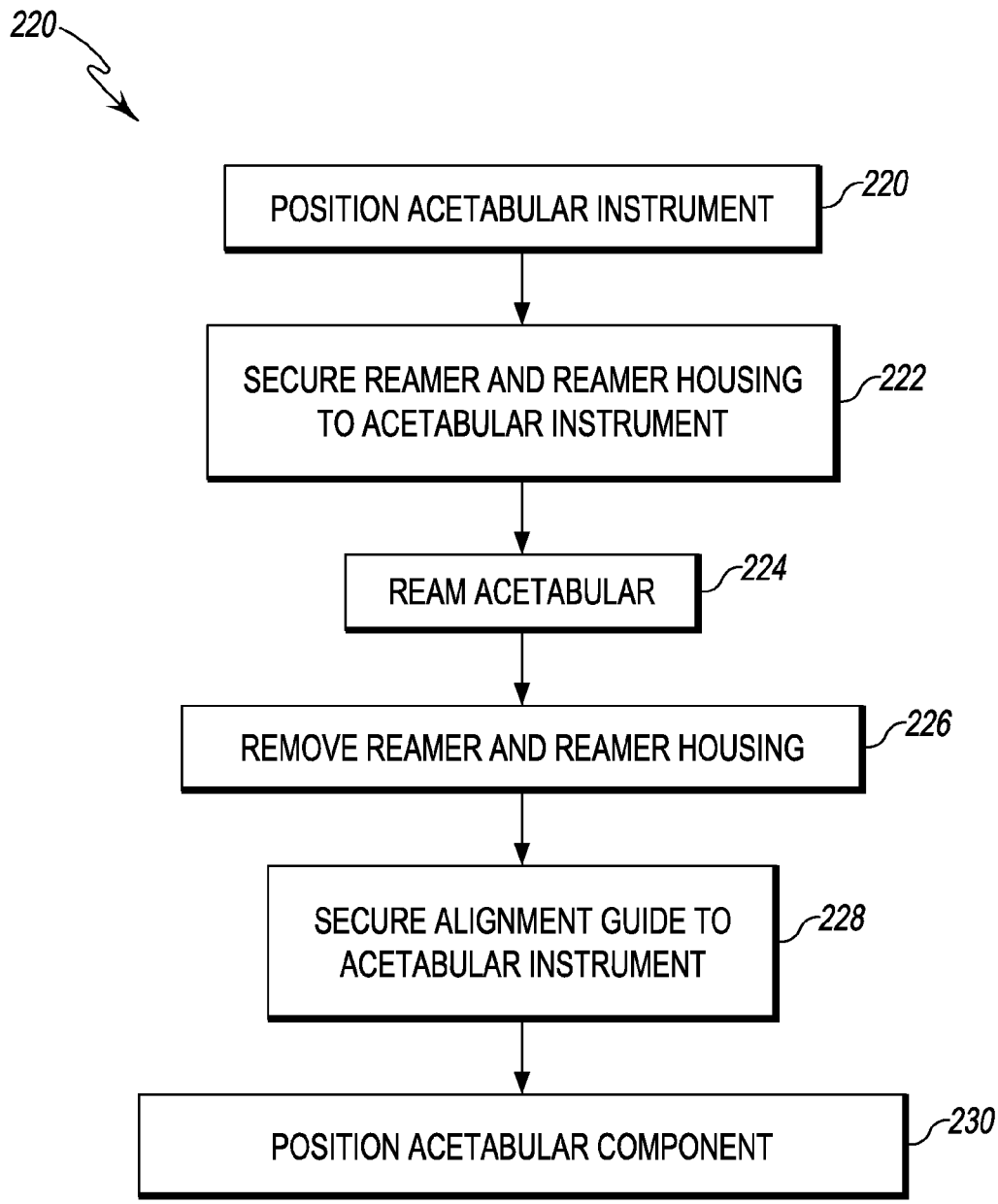
FIG. 9 is a simplified flow diagram of a method of performing an orthopaedic surgical procedure using the acetabular surgical instrument of FIG. 2.

In use, the acetabular surgical instrument 60 is configured to both assist in preparing a patient's acetabulum for surgery and positioning one or more orthopaedic acetabular components 126 in the surgically-prepared acetabulum. Referring to FIG. 9, a method 220 for using the acetabular surgical instrument 60 is shown. The method 220 includes step 222 in which an orthopaedic surgeon positions the acetabular surgical instrument 60 on the patient's coxal bone 136. The acetabular surgical instrument 60 is positioned such that the negative contours 66, 86 of the acetabular surgical instrument 60 receive a portion of the corresponding contour of the patient's coxal bone 136 proximate to the acetabulum. Once the acetabular surgical instrument 60 is positioned on the patient's coxal bone 136, the acetabular surgical instrument 60 may be secured to the coxal bone 136 using one or more bone pins 102.

In step 224, an orthopaedic surgeon secures the reamer 120 and the housing 150 to the acetabular surgical instrument 60. The acetabular surgical instrument 60, the reamer 120, and the housing 150 cooperate to define a predetermined reaming depth. In step 226, the orthopaedic surgeon advances the reamer along the longitudinal axis 118 and reams the patient's acetabulum to a predetermined depth. Before positioning any orthopaedic acetabular components 126 (e.g., trialing components or prosthesis components), in step 228, the orthopaedic surgeon removes the reamer 120 and the housing 150 from the acetabular surgical instrument 60.

In step 230, the orthopaedic surgeon secures the alignment guide 122 to the acetabular surgical instrument 60. The alignment guide 122 defines an alignment axis 128 and is configured to provide a visual indication to the orthopaedic surgeon indicative of the predetermined position and predetermined orientation of the acetabular cup prosthesis 126. As best shown in FIG. 8, the surgical tool 124 and the alignment guide 122 cooperate to provide the visual indication of the predetermined position and orientation. In step 232, the orthopaedic surgeon positions the acetabular cup component 126 by adjusting the surgical tool 124, which is coupled to the acetabular cup component 126, until the surgical tool 124 is aligned with the alignment guide 122.

Figure 10:
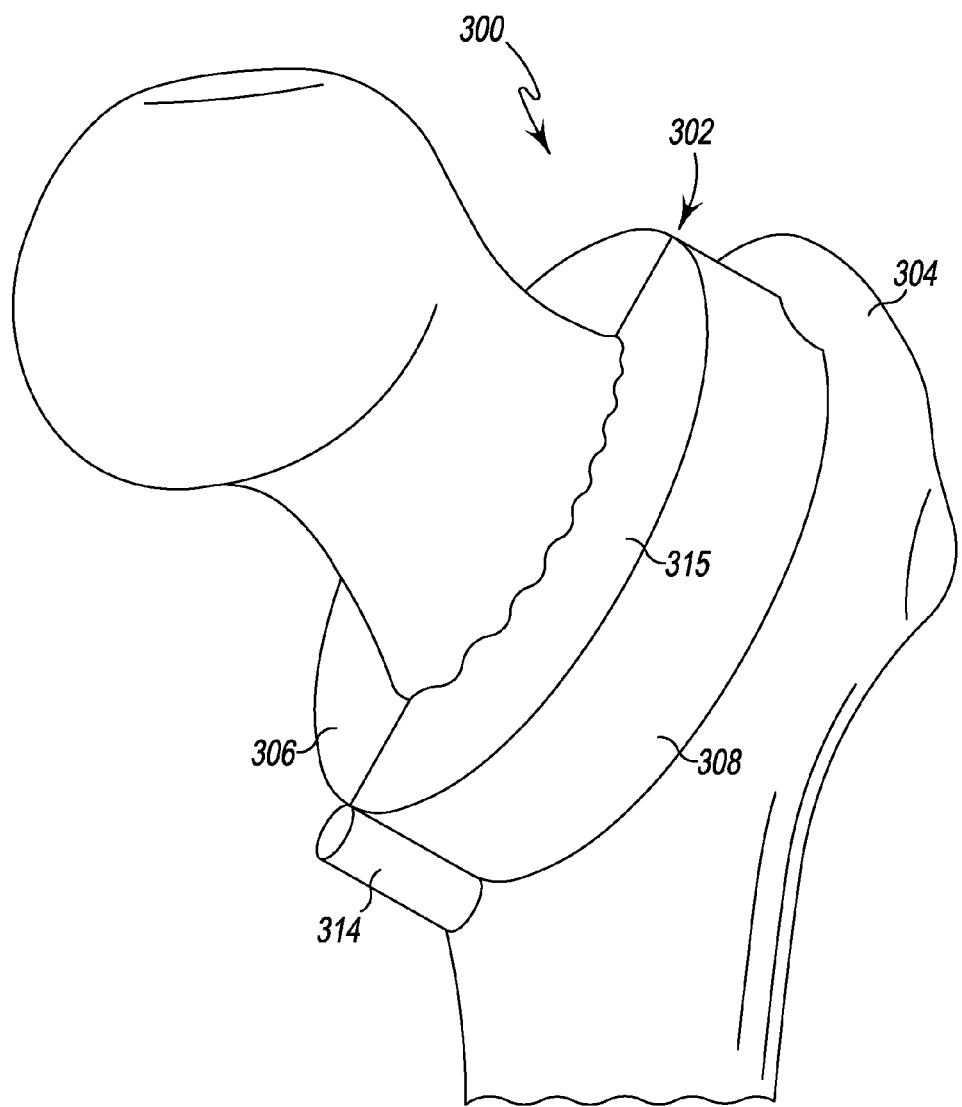
FIG. 10 is a perspective view of the customized patient-specific femoral surgical instrument of FIG. 3 secured to a proximal end of a femur of a patient.
Figure 10:
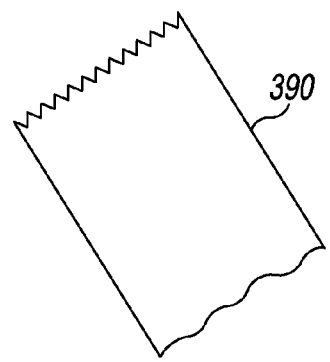

Referring now to FIGS. 3 and 10-15, the femoral surgical instrument 300 includes a collar 302 configured to contact portions of the patient's femur bone 304 during use. In the illustrative embodiment, the collar 302 has a generally annular shape. As is best shown in FIG. 10, the collar 302 is configured to wrap around the neck of the patient's femur bone 304. As best shown in FIG. 3, the collar 302 also includes a top surface 306, an outside surface 308, a bottom surface 310, a bone-facing surface 312, and a hinge 314.

Figure 14:
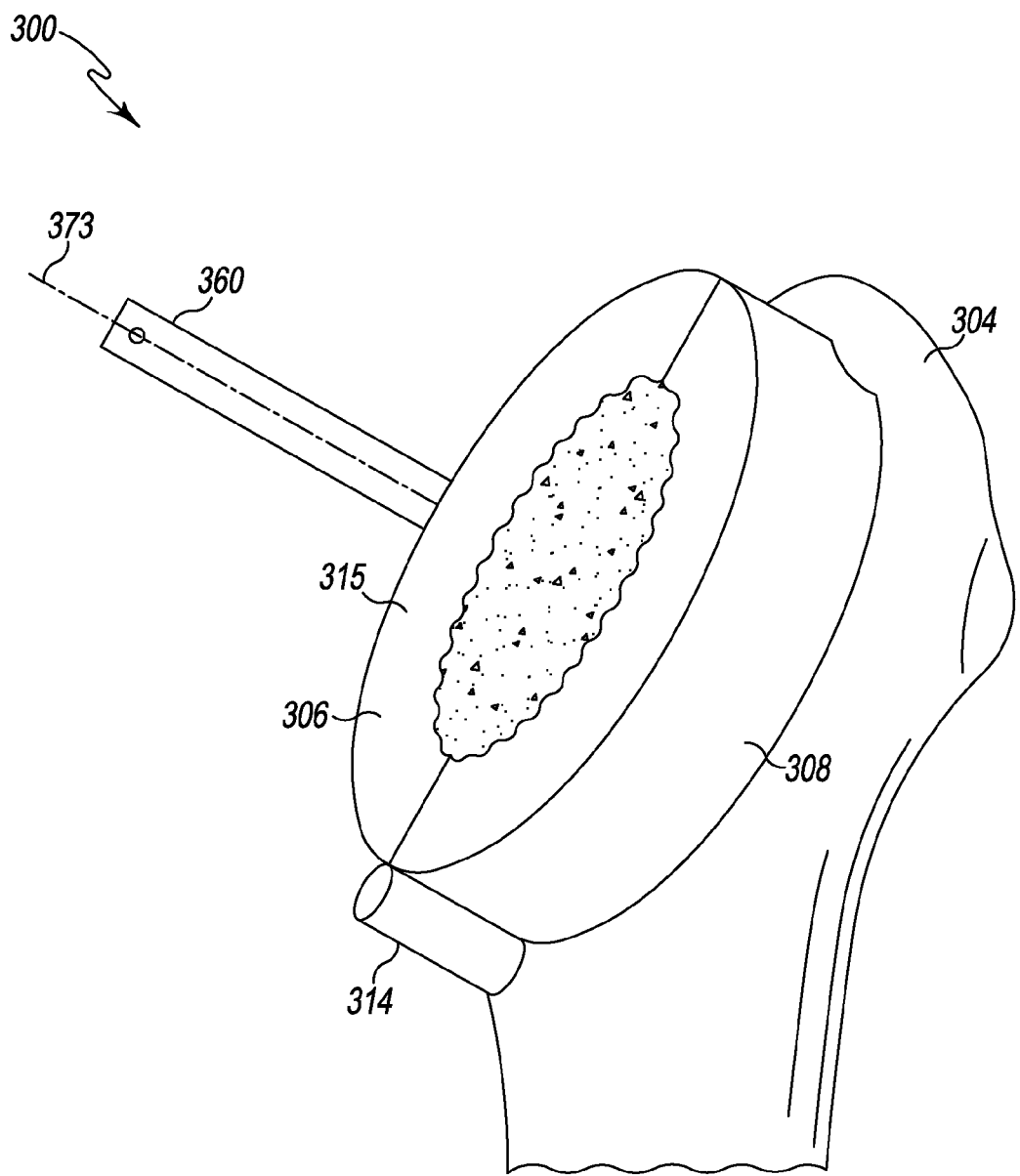
FIG. 14 is a perspective view of the customized patient-specific femoral surgical instrument of FIG. 3 with a portion of the femur resected.

The top surface 306 extends outwardly from an inner edge 316 defined by the bone-facing surface 312 to an outer edge 318 defined by the outside surface 308. The top surface 306 defines a resection plane 315 is configured to guide an orthopaedic resection tool as a portion of the patient's femur bone 304 is resected. A femur bone 304 that has been resected using the femoral surgical instrument 300 is shown in FIG. 14. The resection plane 315 of the top surface 306 is formed based on a predetermined bone resection the orthopaedic surgeon determines during the pre-operative planning. While the illustrative embodiment shows a top surface 306 that is planar, in other embodiments, a blade stop may be formed in the top surface 306. The blade stop may be configured to arrest the movement of a resection tool's blade at a predetermined position. In the illustrative embodiment, the resection plane 315 is defined by the top surface 306, which acts as a non-captured cutting guide. In other embodiments, the resection plane 315 is defined by a captured cutting guide. In some embodiments, to protect a femoral surgical instrument 300 made of a polymer, the top surface 306 may be formed of metal.

In use, an orthopaedic surgeon will position a blade 390 of a resection tool against the top surface 306. The blade 390 will be oriented so that the cut made by the blade 390 will be parallel to the resection plane 315. The surgeon will advance the resection tool along the top surface 306 removing portions of the patient's femur bone 304. Once all of the desired portions of the patient's femur bone 304 have been resected, the orthopaedic surgeon will remove the resection tool. In the illustrative embodiment of FIG. 14, the entire head of the femur bone 304 was resected. In some embodiments, the femoral surgical instrument 300 may be used to make a conservative neck cut on the neck of the femur 304 and a taper is applied to remove the femoral head.

Figure 11:
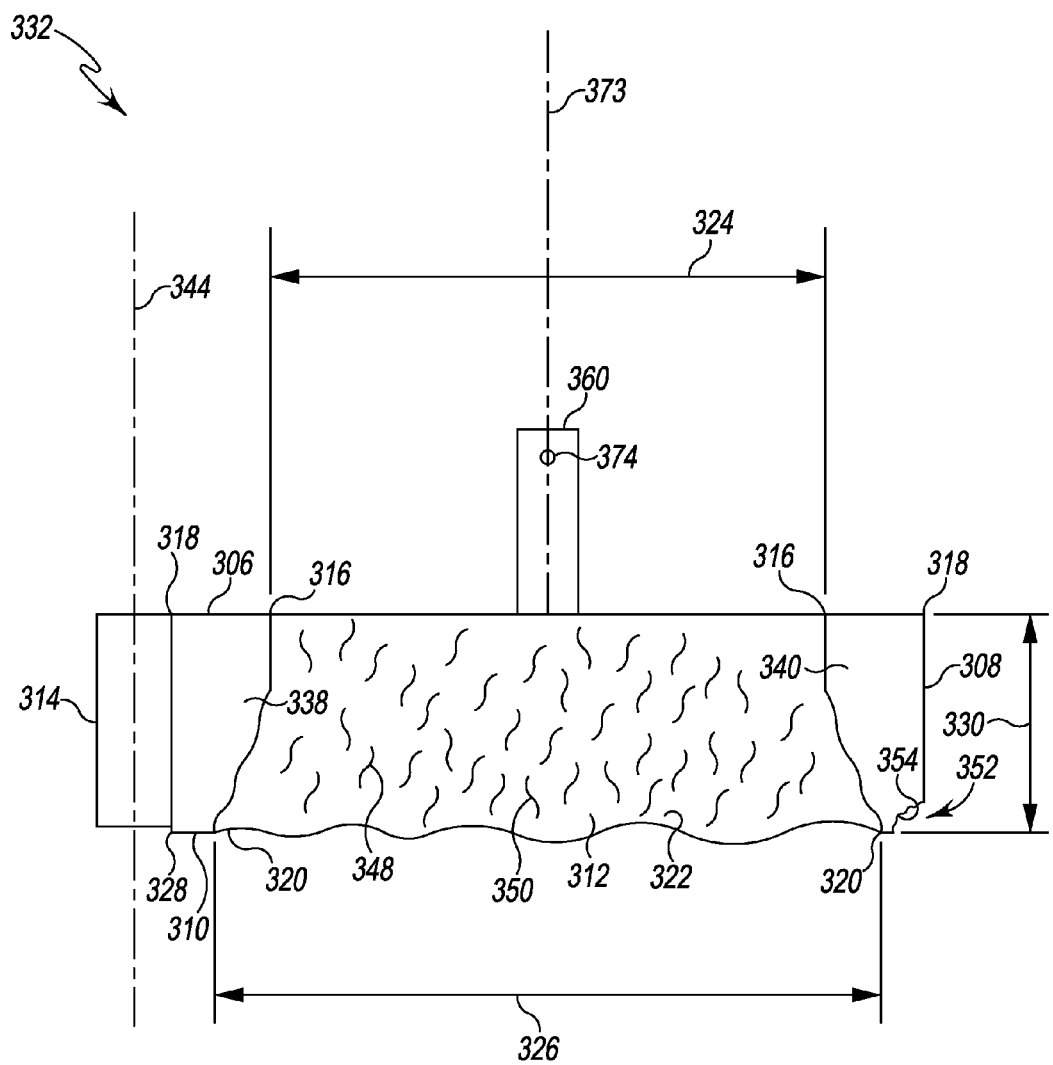
FIG. 11 is a side elevation view of a collar segment of the customized patient-specific femoral surgical instrument of FIG. 3.
Figure 15:
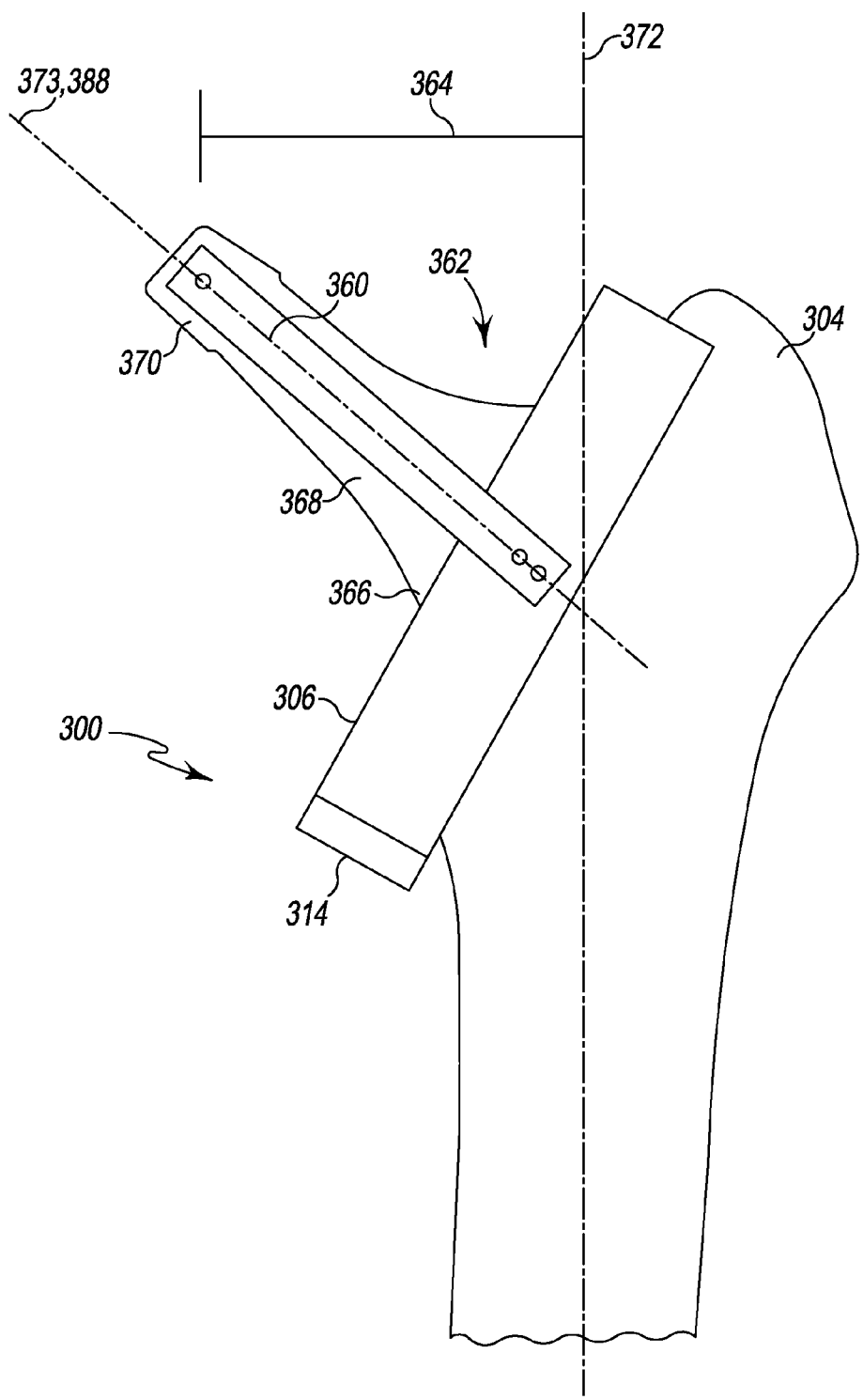
FIG. 15 is a side elevation view of the customized patient-specific femoral surgical instrument of FIG. 3 secured to the femur of a patient and a femoral stem component positioned in the femur.

As best shown in FIG. 11, the bone-facing surface 312 of the femoral surgical instrument 300 extends from the inner edge 316 to a bottom edge 320 defined at the intersection of the bone-facing surface 312 and the bottom surface 310. The bone-facing surface 312 includes a customized patient-specific negative contour 322 configured to receive a corresponding positive contour of the neck of the femur bone 304 and surrounding regions as shown in FIG. 15. The negative contour 322 includes ridges 348 and depressions 350. The ridges 348 correspond to depressions found in the patient's bony anatomy and the depressions 350 correspond to ridges found in the patient's bony anatomy. In this way, the negative contours 322 of the bone-facing surface 312 cooperate to ensure the femoral surgical instrument 300 is placed on the patient's femur bone 304 in a desired position and orientation, which is based on the predetermined offset 364 and the predetermined angle 365 of the femoral stem prosthesis. In other embodiments, the bone-facing surface 312 may include other customized patient-specific negative contours that are configured to receive other corresponding contours of the patient's femur bone 304 proximate to the neck of the femur 304.

At the inner edge 316, the bone-facing surface 312 defines a top inner diameter 324 of the collar 302. The top inner diameter 324 is sized to receive the neck and related portions of the femur bone 304. Since the bone-facing surface 312 conforms to the femur bone 304, the precise distance of the top inner diameter 324 varies according to the shape of the patient's femur bone 304. At the bottom edge 320, the bone-facing surface 312 also defines a bottom inner diameter 326 of the collar 302. The bottom inner diameter 326 being larger than top inner diameter 324, based on the patient's specific bony anatomy.

The outside surface 308 of the collar 302 extends from the outer edge 318 to a lower edge 328 defined at the intersection of the outside surface 308 and bottom surface 310. The outside surface 308 defines a height 330 of the collar 302. The height 330 defines, in part, precise location of the resection plane 315 relative to the patient's femur bone 304. The outside surface 308 of the collar 302 also defines an outer diameter 331 of the collar 302. In other embodiments, a height of the collar 302 may defined as the longitudinal distance between the inner edge 316 and the bottom edge 320. The collar 302 also includes a notch 352 formed in an open end 342 of the femoral surgical instrument. The notch 352 includes a customized patient-specific negative contour 354 having ridges and depressions and configured to receive a positive contour of the patient's femur bone 304.

In the illustrative embodiment, the collar 302 includes a first collar segment 332 and a second collar segment 334. The collar segments 332, 334 are coupled to one another by the hinge 314 positioned at a hinge end 336 of the collar 302.

In other embodiments, the collar 302 does not include a hinge, but rather both of the collar segments 332, 334 may utilize one or more fasteners to secure the collar segments 332, 334 to each other and to the femur 304. Each collar segment 332, 334 extends from a first contacting surface 338, positioned at the hinge end 336, to a second contacting surface 340, positioned at an open end 342 of the collar 302. Each collar segment 332, 334 is arcuate in shape. The second contacting surface 340 of each collar segment 332, 334 is configured to contact the other second contacting surface 340 when the first collar segment 332 and the second collar segment 334 are positioned to form an annular ring.

Figure 12:
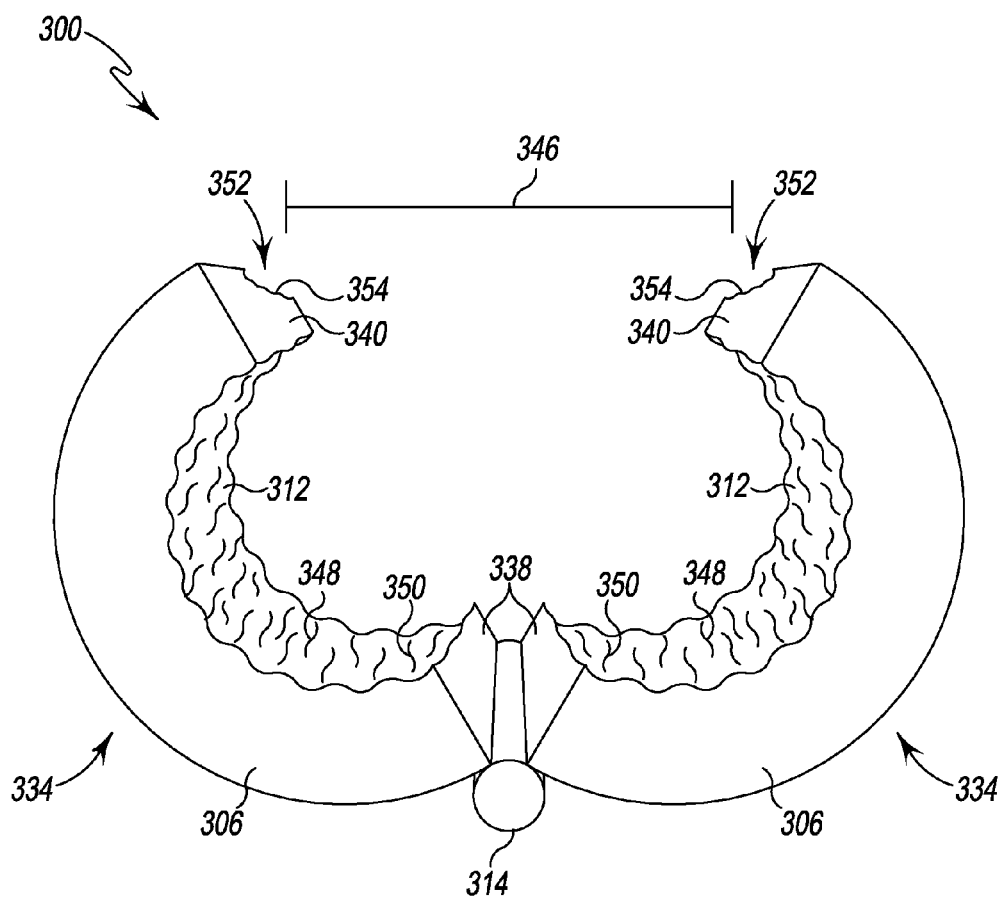
FIG. 12 is a perspective view of the customized patient-specific femoral surgical instrument of FIG. 3 in an opened position.

The hinge 314 interconnects the first collar segment 332 to the second collar segment 334 at the hinge end 336 and is configured to allow each of the collar segments 332, 334 to rotate about a hinge axis 344. The relative rotation of the collar segments 332, 334 allows the collar 302 to rotate between a closed position and an open position. In the closed position, the second contacting surface 340 of each collar segment 332, 334 contacts the other second contacting surface 340 and the collar 302 forms an annular ring as shown in FIG. 3. In the open position, the second contacting surfaces 340 of the collar segments 332, 334 do not contact each other, as shown in FIG. 12. In the open position, a gap 346 is formed between the collar segments 332, 334 at the open end 342 of the collar 302.

To position the collar 302 on the femur bone 304, an orthopaedic surgeon will rotate one of the collar segments 332, 334 until the gap 346 between the collar segments 332, 334 is large enough to allow a portion of the femur bone 304 to pass through. The orthopaedic surgeon will then advance the collar 302 onto the femur bone 304 and position the femur bone 304 to be adjacent to the bone-facing surface 312. Once positioned, the surgeon will rotate the collar segments 332, 334 until the collar is in the closed position. In some embodiments, the collar 302 may be secured in the closed position using methods that are known to one of ordinary skill in the art. For example, the collar 302 may include a friction-fit fastener positioned on the second contacting surfaces 340, a hook and latch fastener positioned on the outside surface 308, adhesive may be applied to the second contacting surfaces 340, the hinge 314 may be configured to generate resistance to keep the collar 302 in the closed position, fasteners, such as screws, and/or any other type of fastening system.

The femoral surgical instrument 300 also includes a customized patient-specific alignment guide 360 removably coupled to the collar 302 as shown in FIG. 3. The alignment guide 360 is configured to provide a visual indication to the orthopaedic surgeon about the planned position and orientation of a femoral stem component 362. In the illustrative embodiment, the femoral stem component 362 is a femoral stem prosthesis configured to be implanted in a patient. In other embodiments, the femoral stem component may be a femoral trialing component. The position and orientation of the alignment guide 360 on the femoral surgical instrument 300 is customized according to the needs of the patient as discussed in greater detail below.

As best shown in FIG. 15, the alignment guide 360 indicates a predetermined offset 364 of the femoral stem component 362 and a predetermined angle 365 of the femoral stem component 362. The femoral stem component 362 includes a body 366, a neck 368 extending superiorly and medially from the body 366, and a trunnion 370 extending superiorly and medially from the neck 368. Trunnion 370 is also configured to receive a femoral head component. The offset 364 is defined as the distance from the center of rotation of the femoral head component to an axis 372 running down the center of the patient's femur bone 304. The predetermined angle 365 is defined as the angle between a trunnion axis 388 and the axis 372.

As shown in FIG. 15, the position and orientation of the femoral stem component 362 may be compared to a predetermined position and orientation using the alignment guide 360. The alignment guide defines an alignment axis 373 extending parallel to the alignment guide 360. In use, the alignment axis 373 defined by the alignment guide 360 is compared to the trunnion axis 388 defined by femoral stem component 362 to determine whether the femoral stem component 362 is positioned in the predetermined position and orientation. If the femoral stem component 362 is not positioned according to the predetermined position and orientation, the orthopaedic surgeon may reposition the femoral stem component 362 until the femoral stem component 362 is in the correct position relative to the alignment guide 360. In some embodiments, the alignment guide 360 includes one or more markings 374 indicative of the planned position and orientation of the femoral stem component 362.

The alignment guide 360 is configured to be removably coupled to the femoral surgical instrument 300. In this way, the alignment guide 360 can be removed to allow other surgical operations to be performed using the femoral surgical instrument 300, such as resecting the femur 304.

Figure 13:
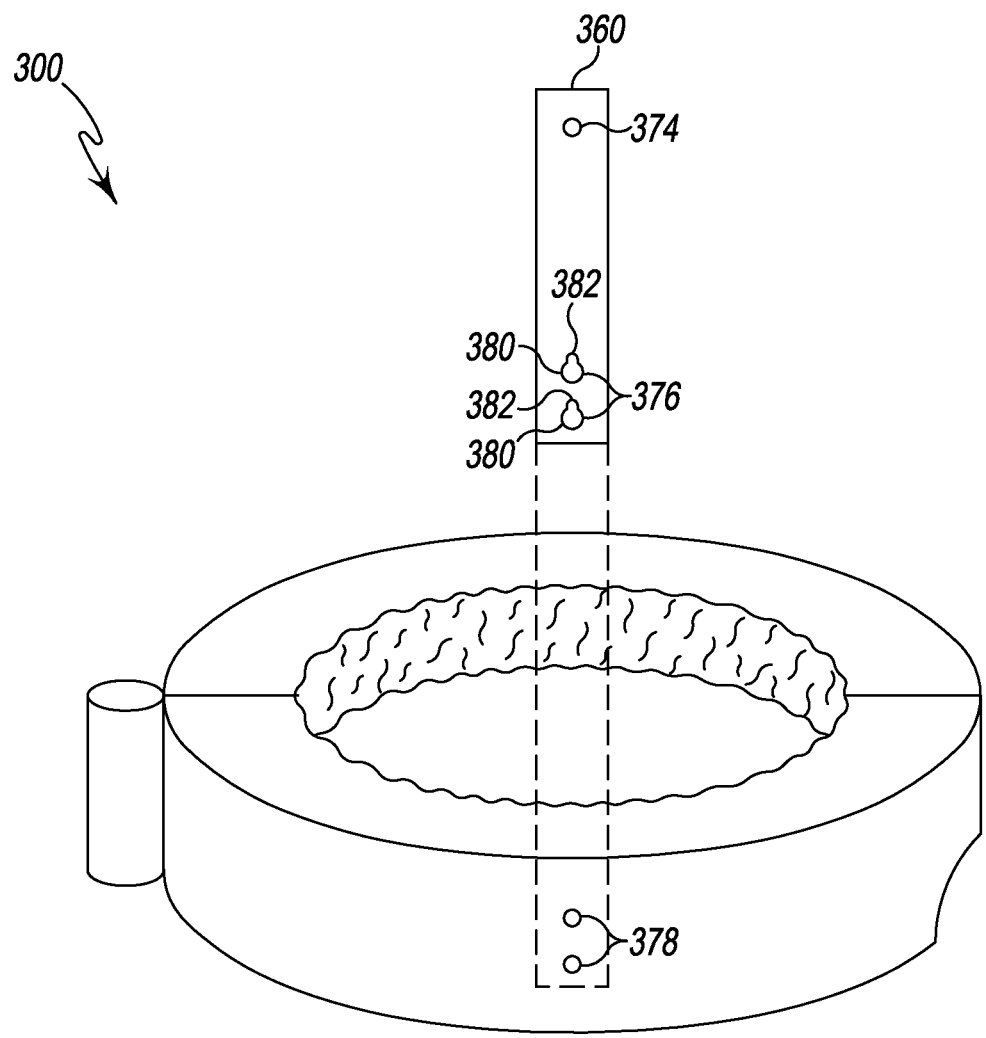
FIG. 13 is an exploded perspective view of the customized patient-specific femoral surgical instrument of FIG. 3.

As shown in FIG. 13, the alignment guide 360 may be coupled to the femoral surgical instrument 300 using a system of flanges and slots. The alignment guide 360 includes two slots 376 that are configured receive a pair of corresponding flanges 378 positioned on the outside surface 308 of the collar 302. Each slot 376 includes an opening 380 and a lip 382. The opening 380 is sized to receive the flange 378 into the slot 376. The lip 382 extends over a part of the slot 376 and is configured to cooperate with the flange 378 to secure the alignment guide 360 to the collar 302. Each flange 378 includes a neck extending away from the outside surface 308 and a top extending away from the outside surface 308. The top having a greater diameter than the neck. In use, each slot 376 is inserted over a corresponding flange 378. The top passing all the way through the opening 380 of the slot 376 of the alignment guide 360. The alignment guide 360 is then advanced such that the lip 382 engages with the top and neck of the flange 378. In this manner, the alignment guide 360 and the collar 302 may be connected in a fixed position relative to the one another. In other embodiments, the alignment guide 360 may be coupled to the collar 302 using other methods known to persons of ordinary skill in the art.

The femoral surgical instrument 300 also includes one or more sensors 384 positioned in the collar 302 configured to indicate the location of the femoral surgical instrument 300 to a computing device. The computing device is similarly embodied as the computing device described above in relation to the acetabular surgical instrument 60. The sensors 384 are positioned in the collar 302 in specific locations based on the predetermined position and orientation of the femoral stem component 362.

The sensors 384 are configured to measure the relative orientation and/or the relative position of the femoral surgical instrument 300 to one or more other sensors positioned elsewhere. For example, the sensors 384 may cooperate with sensors 134 positioned in the acetabular surgical instrument 60 to determine the position of the femoral surgical instrument 300 relative to the acetabular surgical instrument 60. In other examples, the sensors 384 may cooperate with sensors positioned in other surgical instruments, trialing components, prosthetic components, or robotic surgical tools. In some embodiments, the sensors 384 are configured to measure the position and orientation relative to a global reference frame (such as multiple sensor readers set up to perform triangulation of the sensors 384 position).

As shown in FIG. 17, the acetabular surgical instrument 60 and the femoral surgical instrument 300 may cooperate to determine if the assembled hip prosthesis 386 is properly positioned in the patient. Using the sensors 134, 384 on the surgical instruments 60, 300, an orthopaedic surgeon is able to determine the relative locations of the coxal bone 136 and the femur bone 304. With this data, the orthopaedic surgeon is better able to whether the assembled hip prosthesis 386 is positioned correctly before finishing the orthopaedic surgical operation.

The sensors 384 of the femoral surgical instrument 300 are embodied similarly to the sensors 134 of the acetabular surgical instrument 60 described above. The sensors 384 are configured to cooperate with other sensors positioned on the acetabular surgical instrument 60, other surgical instruments (e.g., a broach), and/or orthopaedic components (e.g., trialing components). The sensors 384 determine a bone-coordinate reference frame for the patient's femur 304. Using this bone-coordinate reference frame, the sensors 384 cooperate with other sensors to validate the use of other surgical instruments (e.g., determine broaching depth) and validate the position and orientation of orthopaedic components relative to the femur 304.

Figure 16:
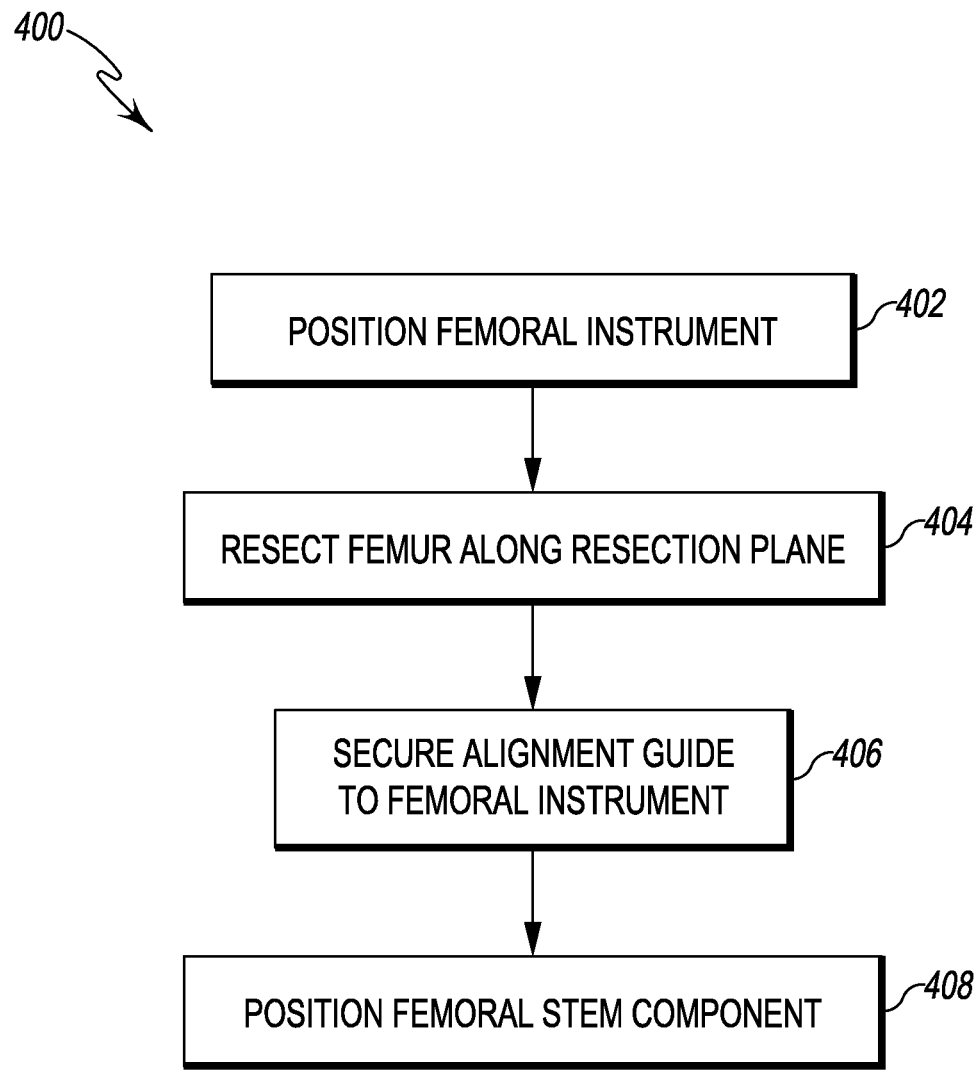
FIG. 16 is a simplified flow diagram of a method of performing an orthopaedic surgical procedure suing the femoral surgical instrument of FIG. 3.

In use, the femoral surgical instrument 300 is configured to both assist in preparing a patient's femur bone 304 for surgery and positioning one or more femoral stem components 362 in the surgically-prepared femur 304. Referring to FIG. 16, a method 400 for using the femoral surgical instrument 300 is shown. The method 400 includes step 402 in which the orthopaedic surgeon positions the femoral surgical instrument 300 on the patient's femur bone 304. The femoral surgical instrument 300 is positioned such that the negative contours 322 bone-facing surface 312 receive a portion of the corresponding positive contour of the patient's femur bone 304.

Once the femoral surgical instrument 300 is positioned on the patient's femur bone 304, in step 404, the orthopaedic surgeon resects the femur 304 using the top surface 306 as a resection guide. As best seen in FIG. 14, the collar 302 may define a resection plane 315 to remove the head of the patient's femur bone 304.

After the femur 304 has been resected and surgically-prepared, in step 406, the orthopaedic surgeon positions the alignment guide 360 on the collar 302 of the femoral surgical instrument 300. In step 408, the orthopaedic surgeon then positions the femoral stem component 362 as shown in FIG. 15. The orthopaedic surgeon uses the alignment guide 360 as a visual guide to assist in the placement of the femoral stem component 362.

Referring to FIG. 17, the surgical instrument system 10 may be used to verify the position of the patient's coxal bone 136 and the patient's femur bone 304 when an assembled hip prosthesis 386 has been implanted in the patient's body. The sensor(s) 134 of the acetabular surgical instrument 60 and the sensor(s) 384 of the femoral surgical instrument 300 are configured to provide position data indicative of the position of the coxal bone 136 and the femur bone 304 to the computing device described above. By comparing the position and orientation data for each of the surgical instruments 60, 300, an orthopaedic surgeon may determine whether the assembled hip prosthesis 386 is positioned correctly. In particular, by knowing the positions of the coxal bone 136 and the femur bone 304, the orthopaedic surgeon may determine what the offset, the leg length, and the range of motion of the patient will be after the orthopaedic surgical operation is complete.

Figure 18:
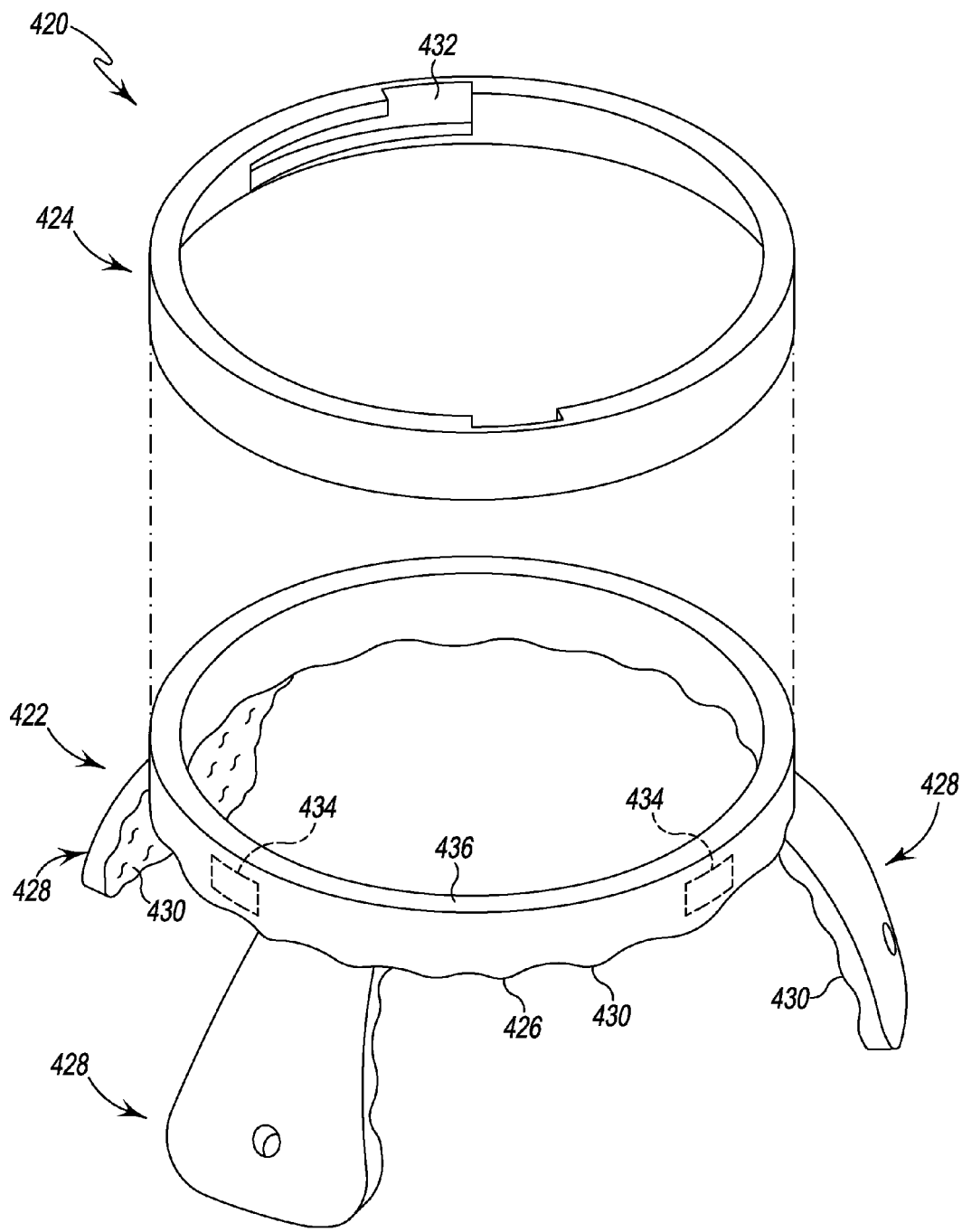
FIG. 18 is an exploded perspective view of another embodiment of a customized patient-specific acetabular surgical instrument.

Referring to FIG. 18, a modular customized patient-specific acetabular surgical instrument 420 is shown. The acetabular surgical instrument 420 includes a low-profile block 422 and an upper ring 424. The low-profile block 422 includes a bottom surface 426, one or more arms 428, and a top surface 436. Both the bottom surface 426 and the arms 428 have negative contours 430 configured to receive a positive contour of the patient's coxal bone 136. In some embodiments, the top surface 436 is configured to assist the surgeon in positioning the acetabular cup component 126 in a predetermined position and orientation. The low-profile block 422 also includes one or more sensors 434. The sensors 434 are embodied similarly to the other sensors described above 134, 384.

In the illustrative embodiment, the upper ring 424 includes attachment features 432. The attachment features 432 are configured to allow other surgical tools (e.g., reamer 120 and housing 150) to couple to the acetabular surgical instrument 420. In some embodiments, an alignment guide 122 may be coupled to the upper ring 424.

In use, the upper ring 424 is detached from the low-profile block 422 before the hip prosthesis is assembled. The smaller size (e.g., the smaller height) of the low-profile block 422 is configured to minimize any interference between the assembled hip prosthesis and the acetabular surgical instrument 420. The sensors 434 of the low-profile block 422 are configured to determine the position of the acetabular surgical instrument 420 relative to other features, such as, for example, sensors on a femoral surgical instrument. In other embodiments, the low-profile block 422 only includes a small portion of the acetabular surgical instrument 420. For example, the low-profile block 422 may only include one of the arms 428 and the one or more sensors 434.

Figure 19:
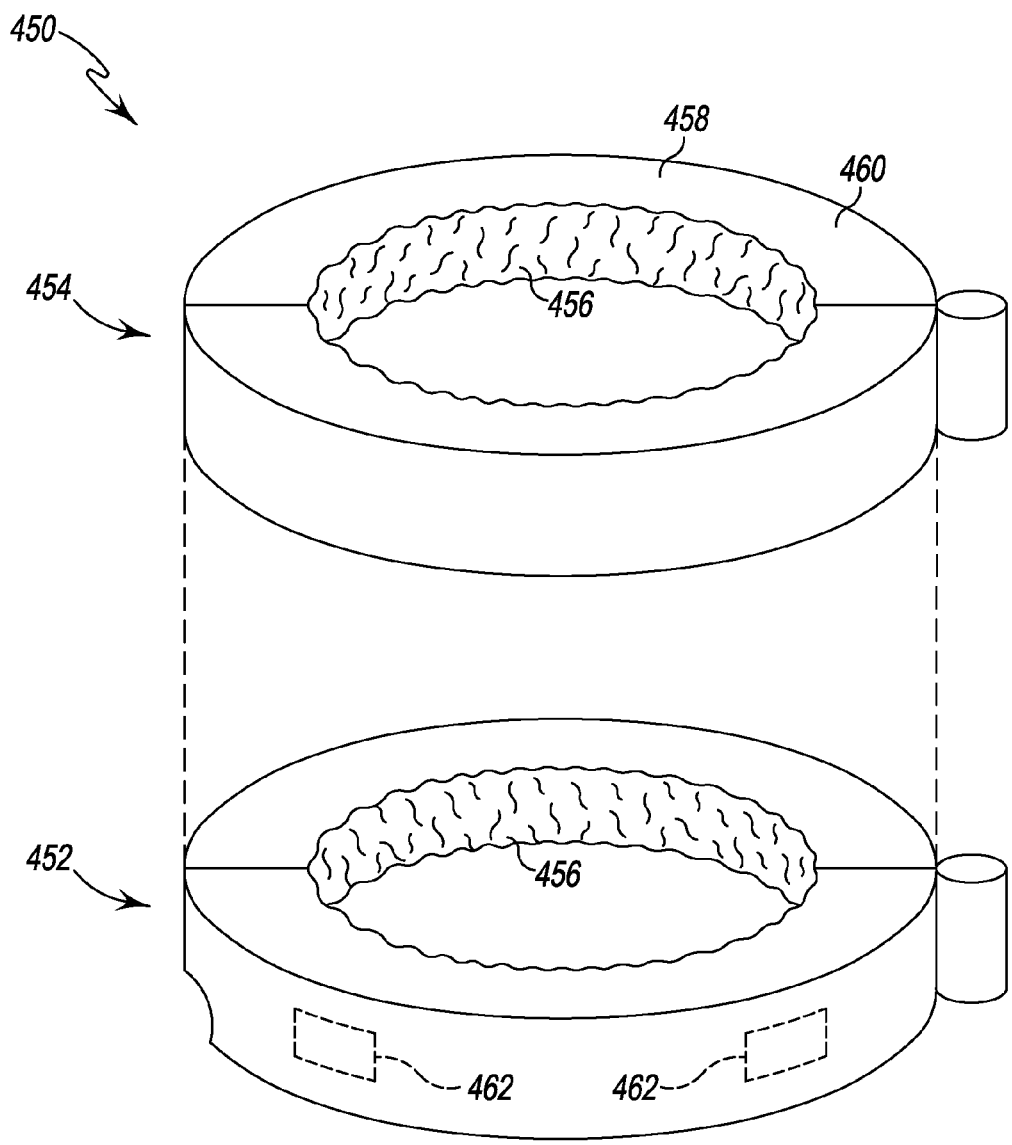
FIG. 19 is an exploded perspective view of another embodiment of a customized patient-specific femoral surgical instrument.

Referring to FIG. 19, a customized patient-specific femoral surgical instrument 450 is shown. The femoral surgical instrument 450 includes a low-profile block 452 and an upper ring 454. Both the low-profile block 452 and the upper ring 454 include a bone-facing surface 456 having a negative contour and configured to receive a positive contour of the patient's femur bone 304. The upper ring 454 includes a top surface 458 that defines a resection plane 460. The upper ring 454 may be used as a resection guide to a surgical resection tool during an orthopaedic procedure. The upper ring 454 is detachable from the low-profile block 452. The low-profile block 452 includes one or more sensors 462 configured to determine the position of the femoral surgical instrument 450.

In use, the upper ring 454 is detached from the low-profile block 452 before the hip prosthesis is assembled. The smaller size (e.g., the smaller height) of the low-profile block 452 is configured to minimize any interference between the assembled hip prosthesis and the femoral surgical instrument 450. The sensors 462 of the low-profile block 452 are configured determine the position of the femoral surgical instrument 450 relative to other features, such as, for example, sensors on a acetabular surgical instrument. The sensors 462 are embodied similarly to the other sensors described above 134, 384. In other embodiments, the low-profile block 452 only includes a small portion of the femoral surgical instrument 450. For example, the low-profile block 452 may be sized to be big enough to only include the sensors 462.

Figure 20:
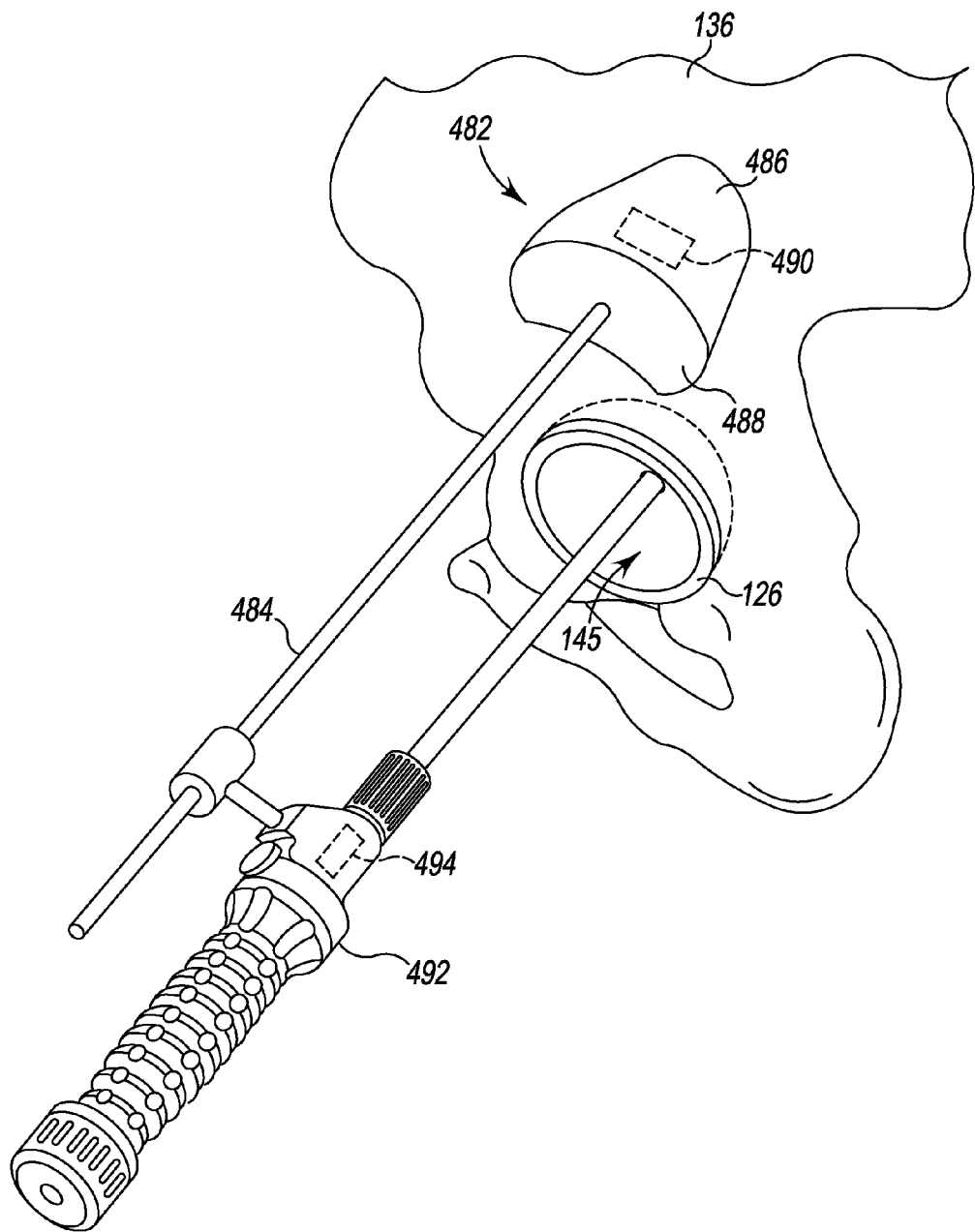
FIG. 20 is a perspective view of another embodiment of a customized patient-specific acetabular surgical instrument.

Referring now to FIG. 20, another embodiment of a customized patient-specific acetabular surgical instrument 480 is shown. The acetabular surgical instrument 480 includes a bone-attachment block 482 and a shaft 484. The bone-attachment block 482 includes a bone-facing surface (not shown), a sidewall 486, and a top wall 488. The bone-facing surfacing of the bone-attachment block 482 has negative contours that correspond to positive contours in the patient's coxal bone 136. The bone-attachment block 482 is configured to be positioned in a specific location on the patient's coxal bone 136 near the acetabulum. The bone-attachment block 482 also includes one or more sensors 490 to determine the precise location of the bone-attachment block 482. The sensors 490 are embodied similarly to the other sensors described above 134, 384.

The shaft 484 extends from the top wall 488 of the bone-attachment block 482 away from the coxal bone 136. The shaft 484 is configured to have one or more surgical instruments 492 attach to the shaft 484. The one or more surgical instruments 492 are supported and guided by the shaft 484 during the orthopaedic surgical operation. The one or more surgical instruments 492 may include a reaming tool or an implant tool. The one or more surgical instruments 492 may also include one or more sensors 494. The one or more sensors 494 are configured to cooperate with the sensors 490 to assist the surgeon in following a pre-operative surgical plan. For example, the sensors 490, 494 may determine when the acetabulum has been reamed to a predetermined depth. In some embodiments, the shaft 484 acts as an alignment guide. For example, the shaft 484 may cooperate with the surgical instruments 492 to ensure that an acetabular component is positioned according to a predetermined position and orientation.

In other embodiments, the acetabular surgical instrument 480 may not include the shaft 484 shown in FIG. 20. In these embodiments, the one or more sensors 490 cooperate with the sensors 494 positioned on the surgical instruments 492, and other orthopaedic equipment, to validate the use of the surgical instruments 492 during an orthopaedic surgical procedure.

Figure 21:
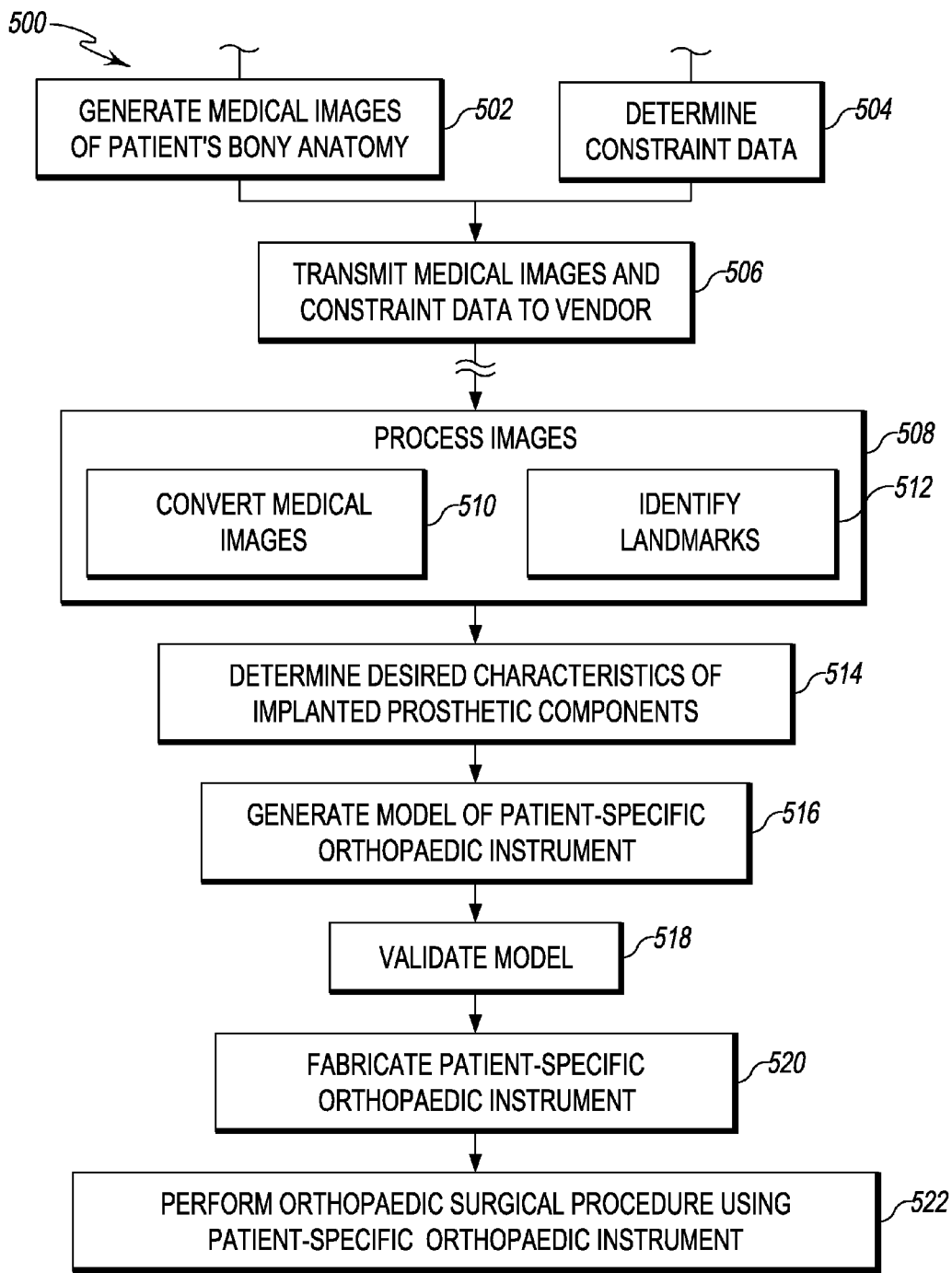
FIG. 21 is a simplified flow diagram of a method for designing and fabricating a customized patient-specific orthopaedic surgical instrument.

Referring to FIG. 21, a method 500 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic components, such as acetabular cup prosthesis, femoral stem prosthesis, or other trialing components.

In some embodiments, the customized patient-specific orthopaedic surgical instrument may be customized to the particular patient based on the location at which the instrument is to be coupled to one or more bones of the patient, such as in an area of the patient's coxal bone proximate to the acetabulum. For example, in some embodiments, the customized patient-specific orthopaedic surgical instrument may include one or more bone-contacting or facing surfaces having a negative contour that matches the contour of a portion of the relevant bone of the patient, which is discussed in more detail below in regard to FIGS. 2 and 3. Illustratively, the customized patient-specific orthopaedic surgical instrument may be embodied as a customized patient-specific acetabular surgical instrument or a customized patient-specific femoral surgical instrument. The customized patient-specific acetabular surgical instrument is configured to be coupled to the patient's coxal bone in a unique location and position with respect to the patient's bony anatomy. That is, the negative contours of the bone-contacting surfaces are configured to receive a matching contour surface of the portion of the patient's coxal bone. Similarly, the customized patient-specific femoral surgical instrument is configured to be coupled to a patient's femur bone in a unique location and position with respect to the patient bony anatomy. That is, the negative contours of the bone-contacting surfaces are configured to receive a matching contour surface of the portion of the patient's femur bone. With these customized patient-specific orthopaedic surgical instruments, the orthopaedic surgeon's guesswork and/or intra-operative decision-making with respect to the placement of the patient-specific acetabular orthopaedic surgical instrument are reduced. For example, the orthopaedic surgeon may not be required to locate landmarks of the patient's bone to facilitate the placement of the patient-specific orthopaedic surgical instrument, which typically requires some amount of estimation on part of the surgeon. Rather, the orthopaedic surgeon may simply couple the customized patient-specific orthopaedic surgical instrument to the patient's coxal bone or femur bone in the unique location. When so coupled, the patient-specific orthopaedic surgical instrument defines particular characteristics of orthopaedic prosthesis relative to the patient's bone. For example, the customized patient-specific acetabular surgical instrument defines a particular degree of version and inclination angles relative to the acetabulum and the intended acetabular orthopaedic prosthesis. In another example, the customized patient-specific femoral surgical instrument defines a location of the offset of the femoral orthopaedic prosthesis relative to the femur.

As shown in FIG. 21, the method 500 includes steps 502 and 504, in which an orthopaedic surgeon performs pre-operative planning of the orthopaedic surgical procedure to be performed on a patient. The steps 502 and 504 may be performed in any order or contemporaneously with each other. In step 502, a number of medical images of the patient's acetabulum and the surrounding bony anatomy are generated. To do so, the orthopaedic surgeon or other healthcare provider may operate an imaging system to generate the medical images. The medical images may be embodied as any number and type of medical images capable of being used to generate a three-dimensional rendered model of the patient's acetabulum and surrounding bony anatomy. For example, the medical images may be embodied as any number of computed tomography (CT) images, magnetic resonance imaging (MRI) images, or other three-dimensional medical images. Additionally, or alternatively, as discussed in more detail below in regard to step 508, the medical images may be embodied as a number of X-ray images or other two-dimensional images from which a three-dimensional rendered model of the area of the patient's coxal bone 136 proximate to the acetabulum and the surrounding bony anatomy may be generated.

In step 504, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for the amount of inclination and version for the acetabular prosthesis, the implant depth of the acetabular prosthesis, the amount of the bone to ream, the size range of the orthopaedic implant, and/or the like. In some embodiments, the orthopaedic surgeon's preferences are saved as a surgeon's profile, which may be used as a default constraint values for further surgical plans.

In step 506, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 508. The orthopaedic surgical instrument vendor or manufacturer processes the medical images to facilitate the determination of the proper planes of inclination and version, implant depth, implant sizing, and fabrication of the customized patient-specific orthopaedic surgical instrument, as discussed in more detail below.

In step 510, the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application.

In step 512, the vendor may process the medical images, and/or the converted/reconstructed images from step 510, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In step 514, the desired characteristics of the orthopaedic prosthesis are determined. For example, the desired inclination plane, the desired version plane, and the desired reaming depth for implantation of the acetabular orthopaedic prosthesis are determined. Each of those variables may be determined based on the type, size, and/or position of the acetabular orthopaedic prosthesis to be used during the orthopaedic surgical procedure; the process images, such as specific landmarks identified in the images; and the constraint data supplied by the orthopaedic surgeon in steps 504 and 506. The type and/or size of the acetabular orthopaedic prosthesis may be determined based on the patient's anatomy and the constraint data. For example, the constraint data may dictate the type, make, model, size, or other characteristic of the acetabular orthopaedic prosthesis. The selection of the acetabular orthopaedic prosthesis may also be modified based on the medical images such that an acetabular orthopaedic prosthesis that is usable with the acetabulum of the patient and that matches the constraint data or preferences of the orthopaedic surgeon is selected. Similarly, the desired implant depth and the femoral head location for implantation of the femoral orthopaedic prosthesis may be determined. The process for determining the variables and characteristics for the femoral orthopaedic prosthesis is similarly embodied as the process described above regarding the acetabular orthopaedic prosthesis.

In addition to the type and size of the orthopaedic prosthesis, the planned location and position of the orthopaedic prosthesis relative to the patient's bony anatomy is determined. To do so, a digital template of the orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's acetabulum or the patient's femur defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's planned characteristics. For example, the planned characteristics of the acetabular orthopaedic prosthesis may include planned inclination and version planes, the planned depth to which the surgeon plans to ream, the orientation of the transverse acetabular ligament and labrum, and other relevant landmarks of the patient's bony anatomy.

Regarding the acetabular surgical instrument, the proper inclination and version planes for the acetabular orthopaedic prosthesis may then be determined based on the determined size, location, and orientation of the acetabular orthopaedic prosthesis. In addition, other aspects of the patient's bony anatomy, as determined in step 512, may be used to determine or adjust the planned inclination and version planes. For example, the determined mechanical axis, landmarks, and/or other determined aspects of the relevant bones of the patient may be used to determine the planned inclination and version planes.

In step 516, a model of the customized patient-specific orthopaedic surgical instrument, which in an illustrative embodiment is a customized patient-specific acetabular orthopaedic surgical instrument, is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The patient-specific orthopaedic surgical instrument to be modeled and fabricated may be determined based on the acetabular orthopaedic surgical procedure to be performed, the constraint data, and/or the type of orthopaedic prosthesis to be implanted in the patient.

The particular shape of the customized patient-specific orthopaedic surgical instrument is determined based on the planned location and implantation angles of the orthopaedic prosthesis relative to the patient's bone. For example, the planned location of the customized patient-specific acetabular orthopaedic surgical instrument relative to the patient's acetabulum may be selected based on, in part, the planned inclination and version planes of the patient's acetabulum as determined in step 514. In another example, the planned location of the customized patient specific femoral orthopaedic surgical instrument relative to the patient's femur may be selected based on, in part, the planned position of the femoral head of the femoral prosthesis. For example, in some embodiments, the customized patient-specific acetabular orthopaedic surgical instrument is embodied as an acetabular reaming guide. In such embodiments, the location of the acetabular reaming guide is selected such that the acetabular reaming guide is usable to position the acetabular orthopaedic prosthesis at the planned inclination and version planes determined in step 514. Additionally, the planned location of the orthopaedic surgical instrument may be based on the identified landmarks of the patient's acetabulum identified in step 512.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the corresponding contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned based on the orthopaedic surgical instrument, as discussed above.

After the model of the customized patient-specific orthopaedic surgical instrument has been generated in step 516, the model is validated in step 518. The model may be validated by, for example, analyzing the rendered model while coupled to the three-dimensional model of the patient's anatomy to verify the correlation the planned characteristics of the orthopaedic surgical instrument and orthopaedic prosthesis, such as inclination and version planes and/or the like. Additionally, the model may be validated by transmitting or otherwise providing the model generated in step 516 to the orthopaedic surgeon for review. For example, in embodiments wherein the model is a three-dimensional rendered model, the model along with the three-dimensional images of the patient's bone may be transmitted to the surgeon for review. In embodiments where the model is a physical prototype, the model may be shipped to the orthopaedic surgeon for validation.

After the model has been validated in step 518, the customized patient-specific orthopaedic surgical instrument is fabricated in step 520. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. The fabricated customized patient-specific orthopaedic instrument is subsequently shipped or otherwise provided to the orthopaedic surgeon. The surgeon performs the orthopaedic surgical procedure in step 522 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Variations in the bony anatomy of the patient may require more than one customized patient-specific acetabular orthopaedic surgical instrument to be fabricated according to the method described herein. For example, the patient may require the implantation of two acetabular orthopaedic prostheses to replace both natural hips. As such, the surgeon may follow the method 500 of FIG. 21 to fabricate a different customized patient-specific acetabular orthopaedic surgical instrument for use in replacing each natural hip. Each customized patient-specific acetabular orthopaedic surgical instrument defines a particular degree of version angle and a particular degree of inclination angle relative to each particular acetabulum that is different due to the variation in the bony anatomy of each hip.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It should be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A system for facilitating implantation of a hip prosthesis, the system comprising:
    a customized patient-specific femoral surgical instrument including a collar sized to fit around a neck of the patient's femur, and a first alignment guide coupled to the collar, the first alignment guide including a first elongated body extending outwardly from the collar,
    an acetabular cup component defining a cup axis extending away from the acetabular cup component, and
    a customized patient-specific acetabular surgical instrument including:
    a body having (i) an inner surface defining a cylindrical passageway configured to receive the acetabular cup component, and (ii) a bone-facing surface having a customized patient-specific negative contour configured to receive a corresponding positive counter of the patient's coxal bone, and
    a second alignment guide coupled to the body, the second alignment guide including a second elongated body extending outwardly from the body and defining an alignment axis positioned to indicate a predetermined position of the acetabular cup component in the patient's coxal bone,
    wherein when the customized patient-specific femoral surgical instrument is coupled to the patient's femur and the customized patient-specific acetabular surgical instrument is coupled to the patient's coxal bone, the first elongated body of the customized patient-specific femoral surgical instrument extends toward the customized patient-specific acetabular surgical instrument and the second elongated body of the customized patient-specific acetabular surgical instrument extends toward the customized patient-specific femoral surgical instrument such that the first alignment guide of the customized patient-specific femoral surgical instrument and the second alignment guide of the customized patient-specific acetabular surgical instrument cooperate to provide a visual indication of a planned position of the hip prosthesis.

2. The system of claim 1, wherein the alignment axis of the alignment guide is positioned according to a predetermined version angle and a predetermined inclination angle of the acetabular cup prosthesis.

3. The system of claim 1, wherein the acetabular cup component includes a base and a body extending away from the base, and the cup axis extends away from the acetabular cup component perpendicular to the base.

4. The system of claim 1, further includes one or more sensors configured to determine a position of the customized patient-specific acetabular surgical instrument relative to the coxal bone, wherein each of the one or more sensors are positioned in the customized patient-specific acetabular surgical instrument based on a predetermined sensor position.

5. The system of claim 4, wherein the one or more sensors cooperate with other sensors positioned on one or more surgical instruments and are configured to determine the position and orientation of the one or more surgical instruments relative to the position and orientation to the patient's femur.

6. The system of claim 4, wherein the one or more sensors are configured to determine the position and an orientation of the customized patient-specific acetabular surgical instrument relative to a customized patient-specific femoral surgical instrument positioned on a patient's femur, wherein the customized patient-specific femoral surgical instrument includes one or more additional sensors configured to interact with the one or more sensors of the customized patient-specific acetabular surgical instrument.

7. The system of claim 1, further comprising:
a femoral stem component defining a trunnion axis extending along a trunnion and a neck of the femoral stem component,
wherein the collar has: (i) a bone-facing surface having a customized patient-specific negative contour configured to receive a corresponding positive counter of the patient's femur, and (ii) a top surface defining a resection plane surface configured to guide a surgical instrument as the patient's femur is resected, and
the alignment guide defines a femoral alignment axis positioned to indicate a predetermined angle of the femoral stem component.

8. The system of claim 7, wherein the alignment guide of the customized patient-specific femoral surgical instrument is positioned to indicate a predetermined offset of the femoral stem component.

* * * * *